United States Patent
Zhang et al.

(10) Patent No.: US 9,737,508 B2
(45) Date of Patent: *Aug. 22, 2017

(54) USE OF NK-1 RECEPTOR ANTAGONISTS IN PRURITUS

(71) Applicant: MENLO THERAPEUTICS INC., Menlo Park, CA (US)

(72) Inventors: Xiaoming Zhang, Sunnyvale, CA (US); Edward F. Schnipper, Redwood City, CA (US); Andrew J. Perlman, Stanford, CA (US); James W. Larrick, Sunnyvale, CA (US)

(73) Assignee: MENLO THERAPEUTICS INC., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/271,103

(22) Filed: Sep. 20, 2016

(65) Prior Publication Data

US 2017/0065558 A1 Mar. 9, 2017

Related U.S. Application Data

(60) Continuation of application No. 15/175,358, filed on Jun. 7, 2016, now Pat. No. 9,474,741, which is a continuation of application No. 14/922,684, filed on Oct. 26, 2015, now Pat. No. 9,381,188, which is a division of application No. 14/312,942, filed on Jun. 24, 2014, now Pat. No. 9,198,898, which is a continuation-in-part of application No. 13/925,509, filed on Jun. 24, 2013, now Pat. No. 8,906,951.

(60) Provisional application No. 61/838,784, filed on Jun. 24, 2013.

(51) Int. Cl.
| | |
|---|---|
| *A61K 31/403* | (2006.01) |
| *A61K 45/06* | (2006.01) |
| *A61K 31/4035* | (2006.01) |
| *A61K 9/00* | (2006.01) |
| *A61K 47/10* | (2017.01) |
| *A61K 9/06* | (2006.01) |
| *A61K 9/20* | (2006.01) |
| *A61K 9/48* | (2006.01) |

(52) U.S. Cl.
CPC .......... *A61K 31/403* (2013.01); *A61K 9/0014* (2013.01); *A61K 9/0053* (2013.01); *A61K 9/06* (2013.01); *A61K 9/2009* (2013.01); *A61K 9/2013* (2013.01); *A61K 9/2018* (2013.01); *A61K 9/2054* (2013.01); *A61K 9/4808* (2013.01); *A61K 9/4858* (2013.01); *A61K 31/4035* (2013.01); *A61K 45/06* (2013.01); *A61K 47/10* (2013.01)

(58) Field of Classification Search
CPC .............. A61K 31/4035; A61K 9/0053; A61K 9/0014; A61K 45/06; A61K 31/403
USPC ................................. 514/171, 416
See application file for complete search history.

(56) References Cited

U.S. PATENT DOCUMENTS

| | | |
|---|---|---|
| 5,077,142 A | 12/1991 | Sakon et al. |
| 5,334,606 A | 8/1994 | MacLeod |
| 5,521,183 A | 5/1996 | Woodward et al. |
| 5,629,327 A | 5/1997 | D'Amato |
| 5,679,360 A | 10/1997 | De Lacharriere et al. |
| 5,869,521 A | 2/1999 | Farrar et al. |
| 5,981,513 A | 11/1999 | Kruse et al. |
| 6,054,445 A | 4/2000 | Zhang et al. |
| 6,221,880 B1 | 4/2001 | Shih |
| 6,476,063 B2 | 11/2002 | Zhang et al. |
| 6,743,793 B2 | 6/2004 | Torisu et al. |
| 7,153,852 B2 | 12/2006 | Torisu et al. |
| 7,217,731 B2 | 5/2007 | Bunda et al. |
| 7,345,083 B2 | 3/2008 | Bunda et al. |
| 7,435,745 B2 | 10/2008 | D'Amato |
| 7,511,072 B2 | 3/2009 | Man et al. |
| 7,544,815 B2 | 6/2009 | Kuethe et al. |
| 7,645,790 B2 | 1/2010 | Bunda et al. |
| 7,683,068 B2 | 3/2010 | Jiang et al. |
| 7,732,479 B2 | 6/2010 | Gazit et al. |
| 7,740,959 B2 | 6/2010 | Yagi |
| 7,893,091 B2 | 2/2011 | Gottesdiener et al. |
| 8,008,479 B2 | 8/2011 | Portman |
| 8,039,488 B2 | 10/2011 | D'Amato |
| 8,124,633 B2 | 2/2012 | DeVita et al. |
| 8,143,283 B1 | 3/2012 | D'Amato |
| 8,153,682 B2 | 4/2012 | Branum et al. |
| 8,263,636 B2 | 9/2012 | Ansorge et al. |

(Continued)

FOREIGN PATENT DOCUMENTS

| | | |
|---|---|---|
| EP | 0717997 A1 | 6/1996 |
| EP | 1711465 A1 | 10/2006 |

(Continued)

OTHER PUBLICATIONS

Aitken, "Section of Measurement in Medicine", Proc Roy Soc Med, vol. 62, pp. 989-993 (Oct. 1969). London, UK: Royal Society of Medicine.

Akiyama, et al., "Roles for substance P and gastrin-releasing peptide as neurotransmitters released by primary afferent pruriceptors", J Neurophysiol, vol. 109, Issue 3, pp. 742-748 (Feb. 2013). Bethesda, MD: American Physiological Society.

Akiyama, et al., Abstract of "Roles for substance P and gastrin-releasing peptide as neurotransmitters released by primary afferent pruriceptors", J Neurophysiol,(2012).

Ally et al., "The use of aprepitant in brachioradial pruritus", Dept. of Dermatology, Stanford University, School of medicine, pp. 1-7 (Dec. 13, 2012).

(Continued)

*Primary Examiner* — Kristin Vajda

(74) *Attorney, Agent, or Firm* — Morrison & Foerster LLP

(57) ABSTRACT

The invention relates to methods for treating pruritus with NK-1 receptor antagonists such as serlopitant. The invention further relates to pharmaceutical compositions comprising NK-1 receptor antagonists such as serlopitant. In addition, the invention encompasses treatment of a pruritus-associated condition with serlopitant and an additional antipruritic agent, and the use of serlopitant as a sleep aid, optionally in combination with an additional sleep-aiding agent.

31 Claims, 5 Drawing Sheets

(56) References Cited

U.S. PATENT DOCUMENTS

| | | |
|---|---|---|
| 8,455,638 B2 | 6/2013 | Bittner et al. |
| 8,809,327 B2 | 8/2014 | Branum et al. |
| 8,889,729 B2 | 11/2014 | Gazit et al. |
| 8,901,307 B2 | 12/2014 | Dakin et al. |
| 8,906,951 B1 | 12/2014 | Zhang et al. |
| 9,198,898 B2 | 12/2015 | Zhang et al. |
| 9,381,188 B2 | 7/2016 | Zhang et al. |
| 2003/0100565 A1 | 5/2003 | Ohmura et al. |
| 2006/0149076 A1 | 7/2006 | Hicks |
| 2009/0209556 A1 | 8/2009 | Bittner et al. |
| 2009/0270477 A1 | 10/2009 | Kuethe et al. |
| 2010/0113469 A1 | 5/2010 | Frenkl et al. |
| 2010/0209496 A1 | 8/2010 | Dokou et al. |
| 2011/0224204 A1 | 9/2011 | Chesworth et al. |
| 2011/0262442 A1 | 10/2011 | Hamilton et al. |
| 2012/0035168 A1 | 2/2012 | Brandl et al. |
| 2012/0077803 A1 | 3/2012 | Stuetz et al. |
| 2012/0225904 A1 | 9/2012 | Bosch et al. |
| 2013/0266645 A1 | 10/2013 | Becker et al. |
| 2013/0303497 A1 | 11/2013 | Hansen et al. |
| 2014/0378521 A1 | 12/2014 | Zhang et al. |
| 2015/0057255 A1 | 2/2015 | Zhang et al. |
| 2016/0038462 A1 | 2/2016 | Zhang et al. |
| 2016/0143882 A1 | 5/2016 | Zhang et al. |

FOREIGN PATENT DOCUMENTS

| | | |
|---|---|---|
| RU | 2370265 C1 | 10/2009 |
| WO | WO 94/20085 A1 | 9/1994 |
| WO | WO 96/06601 | 3/1996 |
| WO | WO 97/14671 | 4/1997 |
| WO | WO 98/19649 A2 | 5/1998 |
| WO | WO 98/19649 A3 | 5/1998 |
| WO | WO 99/02510 A1 | 1/1999 |
| WO | WO 00/56812 A1 | 9/2000 |
| WO | WO 03/026658 A1 | 4/2003 |
| WO | WO 2004/013072 A2 | 2/2004 |
| WO | WO 2004/013072 A3 | 2/2004 |
| WO | WO 2005/032464 A2 | 4/2005 |
| WO | WO 2005/034940 A3 | 4/2005 |
| WO | WO 2005/073191 A1 | 8/2005 |
| WO | WO 2005/090333 A1 | 9/2005 |
| WO | WO 2006/018850 A2 | 2/2006 |
| WO | WO 2006/018850 A3 | 2/2006 |
| WO | WO 2007/002457 A2 | 1/2007 |
| WO | WO 2007/002457 A3 | 1/2007 |
| WO | WO 2007/008564 A1 | 1/2007 |
| WO | WO 2007/044296 A2 | 4/2007 |
| WO | WO 2007/044296 A3 | 4/2007 |
| WO | WO 2007/118651 A1 | 10/2007 |
| WO | WO 2007/146224 A2 | 12/2007 |
| WO | WO 2007/146224 A3 | 12/2007 |
| WO | WO 2008/029168 A2 | 3/2008 |
| WO | WO 2008/029168 A3 | 3/2008 |
| WO | WO 2008/030389 A2 | 3/2008 |
| WO | WO 2008/030389 A3 | 3/2008 |
| WO | WO 2008/054690 A2 | 5/2008 |
| WO | WO 2008/054690 A3 | 5/2008 |
| WO | WO 2008/121268 A1 | 10/2008 |
| WO | WO 2008/124143 A1 | 10/2008 |
| WO | WO 2009/032249 A1 | 3/2009 |
| WO | WO 2009/158467 A2 | 12/2009 |
| WO | WO 2009/158467 A3 | 12/2009 |
| WO | WO 2010/001169 A2 | 1/2010 |
| WO | WO 2010/001169 A3 | 1/2010 |
| WO | WO 2011/057199 A1 | 5/2011 |
| WO | WO 2011/057757 A1 | 5/2011 |
| WO | WO 2011/063233 A1 | 5/2011 |
| WO | WO 2012/009258 A2 | 1/2012 |
| WO | WO 2012/009258 A3 | 1/2012 |
| WO | WO 2012/016569 A1 | 2/2012 |
| WO | WO 2012/017020 A1 | 2/2012 |
| WO | WO 2012/051988 A3 | 4/2012 |
| WO | WO 2012/082580 A2 | 6/2012 |
| WO | WO 2012/082580 A3 | 6/2012 |
| WO | WO 2014/093907 A1 | 6/2014 |
| WO | WO 2014/107794 A1 | 7/2014 |
| WO | WO 2014/209962 A1 | 12/2014 |

OTHER PUBLICATIONS

Amatya, et al., "Responses to intradermal injections of substance P in psoriasis patients with pruritus", Skin Pharmacol Physiol, vol. 23, Issue 3, pp. 133-138 (2010). Basel, Switzerland: S. Karger AG.

American Medical Association, "Statement on a Nonproprietary Name Adopted by the USAN Council", www.ama-assn.org/resources/doc/usan/serlopltant.pdf, p. 1 of 1.

Andersson, et al., "Current pharmacotherapy of lower urinary tract symptoms", Surgery, vol. 29, Issue 6 (Renal and Urology III), pp. 260-264, (2011). St. Louis, MO: Mosby.

Andoh et al., "Substance P induction of Itch-Associated Response Mediation by Cutaneous NK1 Tachykinin Receptors in Mice", The Journal of Pharmacology and Experimental Therapeutics, vol. 286, No. 3, pp. 1140-1145 (1998).

Antiga E, et al., "A further case of subacute prurigo-like linear IgA bullous dermatosis: growing evidence of a new subset," Int J Dermatol., vol. 51, No. 12, pp. 1500-1501 (Dec. 2012). Oxford, UK: Blackwell Science.

Beauregard, et al., "A survey of skin problems and skin care regimens in the elderly", Arch Dermatol,vol. 12, No. 12, pp. 1638-1643 (Dec. 1987). Chicago, IL: American Medical Association.

Bergasa, et al., "Gabapentin in patients with the pruritus of cholestasis: a double-blind, randomized, placebo-controlled trial", Hepatology, vol. 44, No. 5, pp. 1317-1323 (Nov. 2006). Hoboken, NJ: Wiley.

Booken, et al., "Oral aprepitant in the therapy of refractory pruritus in erythrodermic cutaneous T-cell lymphoma" [Correspondence], Br J Dermatol, vol. 164, No. 3, pp. 665-667 (Mar. 2011). Oxford, UK: Wiley-Blackwell.

Brown, et al., "PET [$^{11}$C]DASB imaging of serotonin transporters in patients with alcoholism", Alcohol Clin Exp Res, vol. 31, No. 1, pp. 28-32 (Jan. 2007). Baltimore, MD: Research Society on Alcoholism & Blackwell Publishing.

Carmel, et al., "Management of refractory overactive bladder", Expert Rev Obstet Gynecol, vol. 7, No. 6, pp. 605-613 (Nov. 2012). London, UK: Informa Healthcare.

Chopra, et al., "Neoteric pharmacotherapeutic targets in fibromyalgia", Expert Opin Ther Targets,vol. 15, No. 11, pp. 1267-1281 (Nov. 2011). London, UK: Informa Healthcare.

Costa, et al., Abstract of "How important are NK1 receptors for influencing microvascular inflammation and itch in the skin? Studies using Phoneutria nigriventer venom", Vascul Pharmacol, vol. 45, No. 4, pp. 209-214 (Oct. 2006). New York, NY: Elsevier Science.

Costa, et al "How important are NK1 receptors for influencing microvascular inflammation and itch in the skin? Studies using Phoneutria nigriventer venom", Vascul Pharmacol, vol. 45, No. 4, pp. 209-214 (Oct. 2006). New York, NY: Elsevier Science.

Dalgard, et al., "Self-reported skin morbidity among adults: associations with quality of life and general health in a Norwegian survey", J Investig Dermatol Symp Proc, vol. 9, No. 2, pp. 120-125 (Mar. 2004). Cambridge, MA: Blackwell Science.

Duval et al., "Aprepitant as an antipruritic agent?", N Engl J Med. (Oct. 2009), vol. 361(14):pp. 1415-1416.

Finlay, et al., "Dermatology Life Quality Index (DLQI)—a simple practical measure for routine clinical use", Clinical and Experimental Dermatology, vol. 19, No. 3, pp. 210-216 (May 1994). Los Angeles, CA: OMICS Publishing Group.

Frenkl, et al., "Evaluation of the NK1 receptor antagonist serlopitant in patients with overactive bladder", J Urol, vol. 181, No. 4 Suppl, p. 676 (Apr. 2009). Ridgewood, NJ: Professional Medical Services Co.

Frenkl, et al., "A multicenter, double-blind, randomized, placebo controlled trial of a neurokinin-1 receptor antagonist for overactive bladder", J Urol, vol. 184, No. 2, pp. 616-622 (Aug. 2010). Ridgewood, NJ: Professional Medical Services Co.

(56) References Cited

OTHER PUBLICATIONS

Frenkl, et al., Abstract of "A multicenter, double-blind, randomized, placebo controlled trial of a neurokinin-1 receptor antagonist for overactive bladder", J Urol, vol. 184, No. 2, pp. 616-622 (Aug. 2010). Ridgewood, NJ: Professional Medical Services Co.

Frenkl, et al., "Evaluation of the NK1 receptor antagonist, serlopitant, in patients with overactive bladder: Subgroup analysis by age and disease severity", Eur Urol Suppls, vol. 8, No. 4, p. 676 (Mar. 2009). Amsterdam, Netherlands: Elsevier Science.

George, et al., "Neurokinin 1 receptor antagonism as a possible therapy for alcoholism", Science, vol. 319, pp. 1535-1539 (Mar. 14, 2008). Washington, DC: American Association for the Advancement of Science.

Grundmann, et al., "Chronic Pruritus: Clinics and Treatment", Department of Dermatology, Neurodermatology and Competence Center Pruritus, University of Muenster, Muenster, Germany, Ann Dermatol, vol. 23, No. 1, pp. 1-11, (2011).

Hahn, et al., "Use of the Dermatology Life Quality Index (DLQI) in a midwestern US urban clinic", J Am Acad Dermatol, vol. 45, No. 1, pp. 44-48 (Jul. 2001). St. Louis, MO: Mosby.

Hossen, et al., "Role of Substance P on Histamine H3 Antagonist-Induced Scratching Behavior in Mice", J.Pharmacal. Sci., The Japanese Pharmacological Society, vol. 100, pp. 297-302, (2006).

Huang SC, et al., "Neurokinin-1 receptor antagonists: a comprehensive patent survey", Expert Opin Ther Pat, vol. 20, pp. 1019-1045 (Aug. 2010). London, UK: Informa Healthcare.

Ikoma, Akihiko et al., "The neurobiology of itch", Nature Reviews Neuroscience, (2006), 7(7), pp. 535-547.

Inagaki, et al., Abstract of "Depletion of substance P, a mechanism for inhibition of mouse scratching behavior by tacrolimus", Eur J Pharm, vol. 626, pp. 283-289 (2010). Amsterdam, Netherlands: Elsevier Science.

Inagaki, et al., "Depletion of substance P, a mechanism for inhibition of mouse scratching behavior by tacrolimus", Eur J Pharm, vol. 626, pp. 283-289 (Jan. 25, 2010). Amsterdam, Netherlands: Elsevier Science.

Jiang J. et al., "Potent, brain-penetrant, hydroisoindoline-based human neurokinin-1 receptor antagonists", J Med Chem. (May 2009), vol. 52(9):3039-3046.

Kassick et al., "2-[(3aR,4R,5S,7aS)-5-{(1S)-1-[3,5-bis(trifluoromethyl)phenyl]-2-hydroxyethoxy}-4-(2-methylphenyl)octahydro-2H-isoindol-2-yl]-1,3-oxazol-4(5H)-one: a potent human NK1 receptor antagonist with multiple clearance pathways", J. Med. Chem., vol. 56, No. 14, pp. 5940-5948 (Jul. 2013).

Keller et al., "Lack of efficacy of the substance P (neurokinin$_1$ receptor) antagonist aprepitant in the treatment of major depressive disorder", Biol. Psychiatry, vol. 59, pp. 216-223 (2006).

Klein, P. and Clark R., "An Evidence-Based Review of the Efficacy of Antihistamines in Relieving Pruritus in Atopic Dermatitis", (1999), Arch. Dermatol., vol. 135, pp. 1522-1525.

Kramer et al., "Demonstration of the Efficacy and Safety of a Novel Substance P (NK1) Receptor Antagonist in Major Depression", Neuropsychopharmacology, vol. 29, pp. 385-392 (2004); London, UK: Nature Publishing Group.

Krause, et al., "Effective control of recalcitrant pruritus by bevacizumab: a possible role for vascular endothelial growth factor in chronic itch?" [Letter to the editor], Acta Derm Venereol, (2012)—pub ahead of print.

Krause, et al., "Effective control of recalcitrant pruritus by bevacizumab: a possible role for vascular endothelial growth factor in chronic itch?" [Letter to the editor], Acta Derm Venereol, vol. 93, No. 2, pp. 175-179 (Mar. 27, 2013). Uppsala, Sweden: Society for the Publication of Acta Dermato-Venereologica.

Ladizinski, et al., "Aprepitant: A novel neurokinIn-1 receptor/substance P antagonist as antipruritic therapy in cutaneous T-cell lymphoma", J Am Acad Dermatol, Korea University Ansan Hospital, College of Medicine, Korea University, pp. e198-e199, (Nov. 2012).

Lane, et al., "Brachioradial pruritus: a case report and review of the literature", Cutis, vol. 81, No. 1, pp. 37-40 (Jan. 2008). Parsippany, NJ: Quadrant HealthCom.

Metz, et al., "Chronic pruritus—pathogenesis, clinical aspects and treatment", J Eur Acad Dermatol Venereol, vol. 24, No. 11, pp. 1249-1260 (Nov. 2010). Oxford, UK: Wiley-Blackwell.

Metz, et al., "Chronic pruritus", CME Dermatol, vol. 3, No. 3, pp. 124-143 (Nov. 30, 2008). St. Louis, MO: Mosby.

Meyer et al., "Pruritus in Cutaneous T-cell Lymphomas: Frequent, Often Severe and Difficult to Treat", Acta Derm Venereol, vol. 90, pp. 12-17 (2010).

Michaud, "Couture R. Cardiovascular and behavioural effects induced by naloxone-precipitated morphine withdrawal in rat: characterization with tachykinin antagonists", Neuropeptides, vol. 37, No. 6, pp. 345-354 (Dec. 2003). New York, NY & Edinburgh, Scotland: Churchill Livingstone.

Mir et al., "Aprepitant for pruritus: drug-drug interactions matter", Institut Gustave Roussy, Dept. of Medical Oncology, www.thelancet.com/oncology, vol. 13, pp. 964-965 (Oct. 2012).

Mishra, Santosh K. et al., "The Cells and Circuitry for Itch Responses in Mice", Science, (2013), 340, pp. 968-971.

Murtra, "Rewarding effects of opiates are absent in mice lacking the receptor for substance" [Letter to the editor], Nature, vol. 405, pp. 180-183 (May 11, 2000). Basingstoke, UK: Nature Publishing Group.

Ohmura, et al., "Involvement of substance Pin scratching behaviour in an atopic dermatitis model", European Journal of Pharmacology, vol. 491, Science Direct, pp. 191-194, (2004).

Package insert for EMEND (aprepitant) capsules (Aug. 2013).

Pastor, et al., "The involvement of NK-1 receptor in the behavioural effects of ethanol", Behavioural Pharmacology, vol. 16, Suppl. 1, pp. S20-S20 (2005). London, UK: Lippincott Williams and Wilkins.

Payton, "Urinary incontinence: Neurokinin receptor antagonist inferior to tolterodine for OAB", Nature Rev Urol, vol. 7, No. 8, p. 418 (Aug. 2010). London, UK: Nature Pub. Group.

Phan et al., "Assessment of Pruritus Intensity: Prospective Study on Validity and Reliability of the Visual Analogue Scale, Numerical Rating Scale and Verbal Rating Scale in 471 Patients with Chronic Pruritus", Atopic Dermatitis Urticaria and Itch, Acta Derm Verereol, vol. 92, pp. 502-507 (2012).

Potenzieri, et al, "Basic Mechanisms of Itch", NIH Public Access, Clin Exp Allergy, vol. 42(1), pp. 1-19,(Jan. 2012).

Raap, et al., Abstract of "Pathophysiology of itch and new treatments", Curr Opin Allergy Clin Immunol, vol. 11, No. 5, pp. 420-427 (Oct. 2011). Hagerstown, MD: Lippincott Williams & Wilkins.

Raap, et al., "Pathophysiology of itch and new treatments", Curr Opin Allergy Clin Immunol, vol. 11, No. 5, pp. 420-427 (Oct. 2011). Hagerstown, MD: Lippincott Williams & Wilkins.

Ratti, et al., "Results from 2 randomized, double-blind, placebo-controlled studies of the novel NK1 receptor antagonist casopitant in patients with major depressive disorder", J Clin Psychopharmacol, vol. 31, No. 6, pp. 727-733 (Dec. 2011). Baltimore, MD: Williams and Wilkins.

Ripley, et al., "Lack of self-administration and behavioural sensitisation to morphine, but not cocaine, in mice lacking NK1 receptors", Neuropharmacology, vol. 43, No. 8, pp. 1258-1268 (Dec. 2002). Oxford, UK: Pergamon Press.

Santini D. et al., "Aprepitant for management of severe pruritus related to biological cancer treatments: a pilot study". Lancet Oncol. (Oct. 2012), vol. 13(10):1020-1024.

Schneider, et al., "Psychosomatic cofactors and psychiatric comorbidity in patients with chronic itch", Clin Exp Dermatol, vol. 31, No. 6, pp. 762-767 (Nov. 2006). Oxford, UK: Blackwell Scientific Publications.

Ständer et al., "Clinical Classification of Itch: A Position Paper of the International Forum for the Study of Itch", Acta Derm Venereol, vol. 87, pp. 291-294 (2007).

Ständer et al., "Targeting the Neurokinin Receptor 1 with Aprepitant: A Novel Antipruritic Strategy", Dept of Dermatology, Neurodermatology and Competence Center Pruritus, University of Muenster, Muenster Germany, vol. 5, issue 6, pp. 1-5 (Jun. 2010).

(56) References Cited

OTHER PUBLICATIONS

Ständer et al., "Targeting the Neurokinin Receptor 1 with Aprepitant: A Novel Antipruritic Strategy", (Jun. 2010), PLoS ONE, vol. 5, issue 6, e 10966, pp. 1-6.

Tan-No, et al., Abstract of "Intrathecally administered spermine produces the scratching, biting and licking behaviour in mice", Pain, vol. 86, pp. 55-61 (May 2000). Amsterdam, Netherlands: Elsevier/North-Holland.

Tan-No, et al., "Intrathecally administered spermine produces the scratching, biting and licking behaviour in mice", Pain, vol. 86, pp. 55-61 (May 2000). Amsterdam, Netherlands: Elsevier/North-Holland.

Takada S., et al., "Abberrant epidermal expression of semaphorin 3A and nerve growth factor in prurigo nodularis" [Letter to the editor], J Dermatol., vol. 40, pp. 404-406 (May 2013). London, UK Wiley-Blackwell.

Takeuchi et al., "A Randomized, Open-Label, Multicenter Trial of Topical Tacrolimus for the Treatment of Pruritus in Patients with Atopic Dermatitis", (2012), Ann Dermatol, vol. 24, No. 2, pp. 144-150.

Tey H. L., Yosipovitch G., "Targeted treatment of pruritus: a look into the future", NIH Public Access, Author Manuscript, Br J Dermatol. (Jul. 2011), vol. 165(1):5-17.

Tomillero et al., "Gateways to clinical trials, Summary", Methods Find Exp Clin Pharmacol, vol. 31, No. 5, pp. 341-356 (Jun. 2009). New York, NY: Thomson Reuters.

Tomillero et al., "Gateways to clinical trials, Summary", Methods Find Exp Clin Pharmacol, vol. 32, No. 8, pp. 599-620, (Oct. 2010). New York, NY: Thomson Reuters.

Torres T. et al., "Aprepitant: Evidence of its effectiveness in patients with refractory pruritus continues", J Am Acad Dermatol. (Jan. 2012) 66(1):e14-5.

Tsukumo, et al., "Pharmacological Characterization of Itch-Associated Response Induced by Repeated Application of Oxazolone in Mice", J Pharmacal Sci, The Japanese Pharmacological Society, vol. 113, pp. 225-262 (201 0).

Valet, et al., "Cerebral processing of histamine-induced itch using short-term alternating temperature modulation—an FMRI study", J Invest Dermatol, vol. 128, No. 2, pp. 426-433 (Feb. 2008). Baltimore, MD: Williams & Wilkins.

Veien, et al., "Brachioradial pruritus: a follow-up of 76 patients" [Letter to the editor], Acta Derm Venereol, vol. 91,No. 2, pp. 183-185 (Mar. 2011). Uppsala, Sweden: Society for the Publication of Acta Dermato-Venereologica.

Vincenzi et al., "Aprepitant against Pruritus in patients with solid tumors", Support Care Center, vol. 18, pp. 1229-1230.

Wallengren, J., "Topical Aprepitant in clinical and experimental pruritus", (Aug. 2012), Arc. Dermatol., vol. 148, No. 8, pp. 957-959.

Weidner, et al., "Acute effects of substance P and calcitonin gene-related peptide in human skin—a microdialysis study", J Invest Dermatol, vol. 115, No. 6, pp. 1015-1020 (Dec. 2000). Baltimore, MD: Williams & Wilkins.

Weigelt N, et al., "Prurigo nodularis: systematic analysis of 58 histological criteria in 136 patients," J Cutan Pathol., vol. 37, No. 5, pp. 578-86 (May 2010). Malden, MA: Wiley.

Weisshaar, et al., "Prurigo Nodularis Hepatitis C Infection: Result of an Occupational Disease?" [Letter to the editor], Acta Derm Venereol, vol. 92, pp. 532-533 (2012). Uppsala, Sweden: Society for the Publication of Acta Dermato-Venereologica.

Yosipovitch, et al., "The brain processing of scratching", J Invest Dermatol, vol. 128, No. 7, pp. 1806-1811 (Jul. 2008). New York, NY: Nature Publishing Group.

Yosipovitch G, et al., "Clinical practice. Chronic Pruritus", N Engl J Med., vol. 368, No. 17, pp. 1625-1634 (Apr. 25, 2013). Boston, MA: Massachusetts Medical Society.

Zhang et al., "Activation of Neurokinin-1 Receptors Increases the Excitability of Guinea Pig Dorsal Root Ganglion Cells", J. Pharmacology and Experimental Therapeutics, vol. 343 (1), pp. 44-52, (Jun. 26, 2012).

Invitation to pay additional fees with partial international search report received in connection with international application No. PCT/US2014/043811; mailed Sep. 17, 2014.

USE OF NK-1 RECEPTOR ANTAGONISTS IN PRURITUS

CROSS REFERENCE TO RELATED APPLICATIONS

The present application claims priority to and the benefit of U.S. patent application Ser. No. 13/925,509 and U.S. Provisional Patent Application No. 61/838,784, both filed on Jun. 24, 2013.

TECHNICAL FIELD

The invention relates to methods for treating acute or chronic pruritus with an NK-1 receptor antagonist. The invention further relates to pharmaceutical compositions comprising an NK-1 receptor antagonist.

BACKGROUND OF THE INVENTION

Pruritus, or itch, is an uncomfortable skin sensation that provokes a desire to scratch. Although itch may be acute, for example, from an insect sting, chronic pruritus originates from many different causes. It is a seriously debilitating condition, comparable to chronic pain, which negatively impacts quality of life.

Chronic pruritus affects millions of people worldwide, although solid epidemiological data is very limited. For example, one study reported that 8-10% of the population of Oslo suffer from chronic pruritus from all causes (F. Dalgard et al., *J. Investig. Dermatol. Symp. Proc.*, 2004, 9(2):120-5). Patients with certain diseases and conditions report high incidences of chronic itch, including those with psoriasis (78-84%), Hodgkin's disease (25-35%), dialysis patients (22%), and polycythaemica vera (48%) (M. Metz and S. Ständer, *CME Dermatol.*, 2008; 3(3):124-143). Chronic pruritus is also a prevalent symptom in cutaneous T-cell lymphoma (68-93%), a disease that includes mycosis fungoides and Sézary syndrome (N. Meyer et al., *Acta Derm. Venereol.*, 2010, 90:12-17). Pruritus is the most common dermatological complaint in elderly patients (S. Beauregard and B. A. Gilchrest, *Arch. Dermatol.*, 1987, 123:1638-43). Itch is often the side effect of certain drugs, such as EGF receptor antagonists.

Antihistamines can sometimes effectively treat itch due to acute urticaria, but many chronic pruritic diseases respond poorly to conventional H1 receptor antagonists (Tey H. L. and G. Yosipovitch; *Br. J. Dermatol.*, 2011, 165(1):5-17). In addition to marginal efficacy, antihistamines can also cause intolerable drowsiness. Other current therapies possess various limitations. For example, anticonvulsants such as gabapentin inhibit spinal mechanisms in the perception of itch, but their use is limited due to their slow onset of action (5-6 weeks) (Metz and Ständer, 2008). Opiate receptor antagonists such as naloxone, nalmefene, and naltrexone decreased pruritus symptoms in patients with liver and kidney disease, although significant central nervous and gastrointestinal side effects occurred (Metz and Ständer, 2008; N. V. Bergasa et al., *Hepatology*, 2006, 44(5):1317-23).

Substance P, the endogenous ligand for the neurokinin-1 (NK-1) receptor, is a significant mediator of pruritus (T. Andoh et al., *J. PharmacoL Exp. Ther*, 1998, 286:1140-5). Intradermal injection of substance P elicits an itch sensation in human subjects, and an associated itch response in mice. The substance P-induced itch—associated response in mice is not inhibited by antihistamines (B. Amatya et al., *Skin Pharmacol. Physiol.*, 2010; 23:133-138; C. Weidner et al., *J. Invest. Dermatol.*, 2000, 115:1015-1020). In an experiment designed to study the role of substance P in pruritus, Ohmura et al. reported that tachykinin NK-1 receptor antagonist, BIIF 1149 CL, inhibited scratching behavior in a picryichloride-induced dermatitis model in NC/Nga mice (*Eur. J. Pharmacol.*, 2004, 491:191-194; U.S. Patent Application No. 2003/100565).

Aprepitant (Emend®), an NK-1 receptor antagonist, is approved by the FDA for use in the prevention of chemically induced nausea and vomiting (emesis) after chemotherapy. Duval and Dubertret first reported that oral aprepitant (80 mg daily) had utility in treating pruritus in three patients with Sézary syndrome (*N. Engl. J. Med.*, 2009, 361(14): 1415-6). Torres et al. disclosed similar results (*J. Am. Acad. Dermatol.*, 2012; 66(1):e14-5). Stander et al. conducted a small, open-label study which demonstrated that aprepitant significantly decreased chronic pruritus caused by conditions such as atopic diathesis and prurigo nodularis. In this study, twenty previously untreatable patients were given a daily dose of 80 mg for 3 to 13 days. Eighty percent of the patients experienced a considerable reduction in itch intensity (S. Ständer, et al., *PLoS One*, 2010, 5:6, el 0968). However, Wallengren conducted a follow-up double-blind study based on Standees work testing a single dose of topical aprepitant blended at a 5% concentration in a lipophilic vehicle in patients suffering from chronic pruritus of various etiologies. Although the drug was absorbed into the skin, the patients' itch was not alleviated (J. Wallengren, *Arch. Dermatol.*, 2012, 148(8):957-9).

Although oral aprepitant is generally well-tolerated, it is extremely expensive, limiting its use in chronic pruritus (Tey, 2011). Further, aprepitant is a moderate inhibitor as well as an inducer of CYP3A4 and CYP2C9, indicating that drug-drug interactions with chemotherapeutic agents and corticosteroids must be considered (Torres, 2012). Mir and Coriat have suggested that the risk of drug-drug interactions with aprepitant is high because it can alter the activity of cytochrome P450 3A4 isoform (CYP-3A4), an enzyme involved in the metabolism of a range of commonly prescribed drugs, including tyrosine-kinase inhibitors, either inducing or inhibiting the CYP-3A4, depending on which drugs are given concomitantly. Tyrosine-kinase inhibitors do not induce frequent nausea and emesis; therefore, clinical experience with concomitant administration of aprepitant and these drugs is scarce. Furthermore, the pharmacokinetics of tyrosine-kinase inhibitors varies widely between patients, and drug-drug interactions are common (O. Mir and R. Coriat, *The Lancet*, 2012, 13:964-965). Thus, the need for additional, safe treatments for acute and chronic pruritus exists.

SUMMARY OF THE INVENTION

In one aspect, this invention provides a method of treating pruritus in a patient in need of such treatment comprising administering to said patient a therapeutically effective amount of 3-[(3aR,4R,5S,7aS)-5-[(1R)-1-[3,5-bis(trifluoromethyl)phenyl]ethoxy]-4-(4-fluorophenyl)-1,3,3a,4,5,6,7, 7a-octahydroisoindol-2-yl]cyclopent-2-en-1-one or a pharmaceutically acceptable salt, solvate or polymorph thereof. In one embodiment, the therapeutically effective amount comprises a dosage of 0.10 mg, 0.15 mg, 0.20 mg, 0.25 mg, 0.5 mg, 0.75 mg, 1 mg, 2 mg, 2.5 mg, 3 mg, 4 mg, 5 mg, 6 mg, 7 mg, 8 mg, 9 mg, 10 mg, 15 mg, 20 mg, 25 mg, or 30 mg one or more times a day. In another embodiment, the therapeutically effective amount comprises a dosage of 0.25 mg, 1 mg, or 5 mg once a day. In a further embodiment, the therapeutically effective amount comprises a dosage of from about 0.1 mg to about 30 mg or from about 1 mg to about 7.5 mg. In another embodiment, the therapeutically effective amount is administered orally in the form of a tablet. In a further embodiment, the therapeutically effective amount is administered once a day at bedtime. In another embodiment, the therapeutically effective amount is administered once a day, once every other day, once every third day, once every fourth day, or once a week. In other embodiments, serlopitant is administered under a chronic dosing regimen. In some embodiments, a therapeutically effective amount of serlopitant is administered over a period of at least 2 weeks, 3 weeks, 1 month, 1.5 months, 2 months, 3 months, 4 months, 5 months, 6 months or longer.

In another aspect, this invention provides a method of treating pruritus whereby 3-[(3aR,4R,5S,7aS)-5-[(1R)-1-[3,5-bis(trifluoromethyl)phenyl]ethoxy]-4-(4-fluorophenyl)-1,3,3a,4,5,6,7,7a-octahydroisoindol-2-yl]cyclopent-2-en-1-one (serlopitant) or a pharmaceutically acceptable salt, solvate or polymorph thereof is administered to a patient in need of such treatment according to a schedule, wherein a least one loading dose is first administered, and, second, at least one therapeutically effect maintenance dose is administered. In one embodiment, the loading dose is five times, four times, three times, or two times the maintenance dose. In another embodiment, the loading dose is three times the maintenance dose. In a further embodiment, the loading dose is administered on day 1 and the maintenance dose is administered on day 2 and thereafter. In another embodiment, the loading dose and the maintenance dose are administered at bedtime. In another embodiment, the method further comprises administering a second loading dose prior to administering the maintenance dose. In one embodiment, the loading dose is three times the maintenance dose and the second loading dose is two times the maintenance dose. In a further embodiment, the therapeutically effective maintenance dose is 0.10 mg, 0.15 mg, 0.20 mg, 0.25 mg, 0.5 mg, 0.75 mg, 1 mg, 2 mg, 2.5 mg, 3 mg, 4 mg, 5 mg, 6 mg, 7 mg, 8 mg, 9 mg, 10 mg, 15 mg, 20 mg, 25 mg, or 30 mg administered one or more times a day. In another embodiment, the therapeutically effective maintenance dose comprises a dosage of 0.25 mg, 1 mg, or 5 mg administered once a day. In a further embodiment, the therapeutically effective maintenance dose comprises a dosage from about 0.1 mg to about 30 mg or from about 1 mg to about 7.5 mg. In another embodiment, the therapeutically effective maintenance dose is administered once a day, once every other day, once every third day, once every fourth day, or once a week. In other embodiments, serlopitant is administered under a chronic dosing regimen. In some embodiments, a therapeutically effective maintenance dose of serlopitant is administered over a period of at least 2 weeks, 3 weeks, 1 month, 1.5 months, 2 months, 3 months, 4 months, 5 months, 6 months or longer. In certain embodiments, serlopitant is administered orally.

In one aspect, this invention provides a pharmaceutical composition for the treatment of pruritus comprising 3-[(3aR,4R,5S,7aS)-5-[(1R)-1-[3,5-bis(trifluoromethyl)phenyl]ethoxy]-4-(4-fluorophenyl)-1,3,3a,4,5,6,7,7a-octahydroisoindol-2-yl]cyclopent-2-en-1-one or a pharmaceutically acceptable salt, solvate or polymorph thereof and a pharmaceutically acceptable carrier. In one embodiment, the pharmaceutical composition is formulated as a tablet comprising Compound 1 or a pharmaceutically acceptable salt, solvate or polymorph thereof and one or more diluents, disintegrants, surfactants or lubricants. In another embodiment, the composition comprises a capsule filled with a solution comprising Compound 1 or a pharmaceutically acceptable salt, solvate or polymorph thereof and an amphiphilic agent. In a further embodiment, the amphiphilic agent is a fatty acid ester of glycerol, propylene glycol or sorbitol. In another embodiment, the pharmaceutical composition comprises 0.10 mg, 0.15 mg, 0.20 mg, 0.25 mg, 0.5 mg, 0.75 mg, 1 mg, 2 mg, 2.5 mg, 3 mg, 4 mg, 5 mg, 6 mg, 7 mg, 8 mg, 9 mg, 10 mg, 15 mg, 20 mg, 25 mg, or 30 mg of Compound 1 or a pharmaceutically acceptable salt, solvate or polymorph thereof. In another embodiment, the composition comprises 0.25 mg, 1 mg, or 5 mg of Compound 1 or a pharmaceutically acceptable salt, solvate or polymorph thereof.

In another aspect, this invention provides a method of treating acute or chronic pruritus in a patient in need of such treatment comprising administering to said patient a therapeutically effective amount of a pharmaceutical composition comprising 3-[(3aR,4R,5S,7aS)-5-[(1R)-1-[3,5-bis(trifluoromethyl)phenyl]ethoxy]-4-(4-fluorophenyl)-1,3,3a,4,5,6,7,7a-octahydroisoindol-2-yl]cyclopent-2-en-1-one or a pharmaceutically acceptable salt, solvate or polymorph thereof and a pharmaceutically acceptable carrier. In one embodiment, the method involves treatment with a pharmaceutical composition formulated as a tablet comprising Compound 1 or a pharmaceutically acceptable salt, solvate or polymorph thereof and one or more diluents, disintegrants, surfactants or lubricants. In another embodiment, the method involves administration of a composition comprising a capsule filled with a solution comprising Compound 1 or a pharmaceutically acceptable salt, solvate or polymorph thereof and an amphiphilic agent. In a further embodiment, the amphiphilic agent is a fatty acid ester of glycerol, propylene glycol or sorbitol. In another embodiment, the method involves treatment with a pharmaceutical composition comprising 0.10 mg, 0.15 mg, 0.20 mg, 0.25 mg, 0.5 mg, 0.75 mg, 1 mg, 2 mg, 2.5 mg, 3 mg, 4 mg, 5 mg, 6 mg, 7 mg, 8 mg, 9 mg, 10 mg, 15 mg, 20 mg, 25 mg, or 30 mg of Compound 1 or a pharmaceutically acceptable salt, solvate or polymorph thereof. In another embodiment, the composition comprises 0.25 mg, 1 mg, or 5 mg of Compound 1 or a pharmaceutically acceptable salt, solvate or polymorph thereof.

In a further embodiment, a pruritus-associated condition is treated by administration of serlopitant (Compound 1) and an additional antipruritic agent. In a still further embodiment, a sleep problem or disorder is treated by administration of serlopitant, optionally in combination with an additional sleep-aiding agent.

Other objects of the invention may be apparent to one skilled in the art upon reading the following specification and claims.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
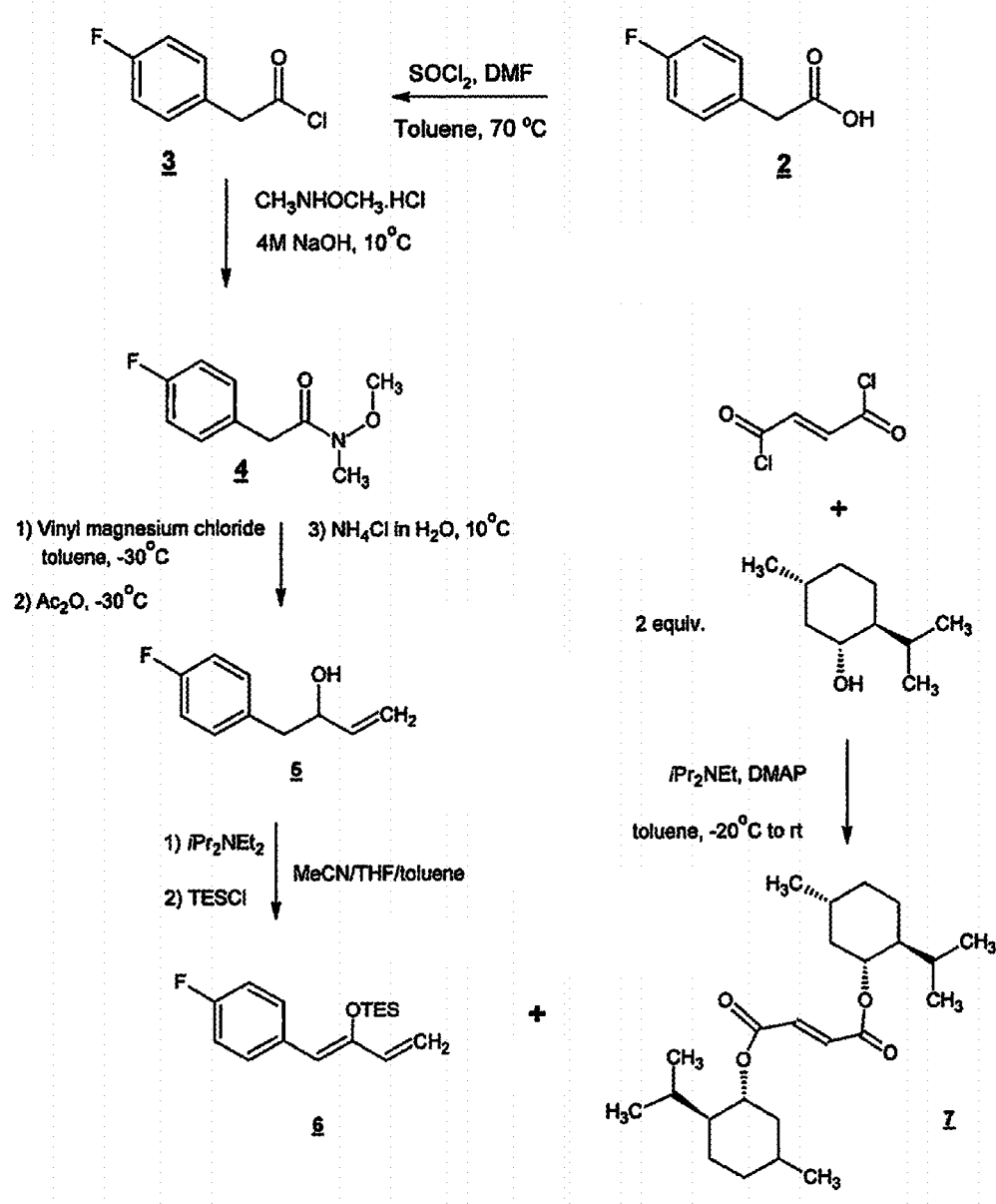
FIG. 1 depicts a synthetic scheme for serlopitant, Compound 1.
Figure 1:
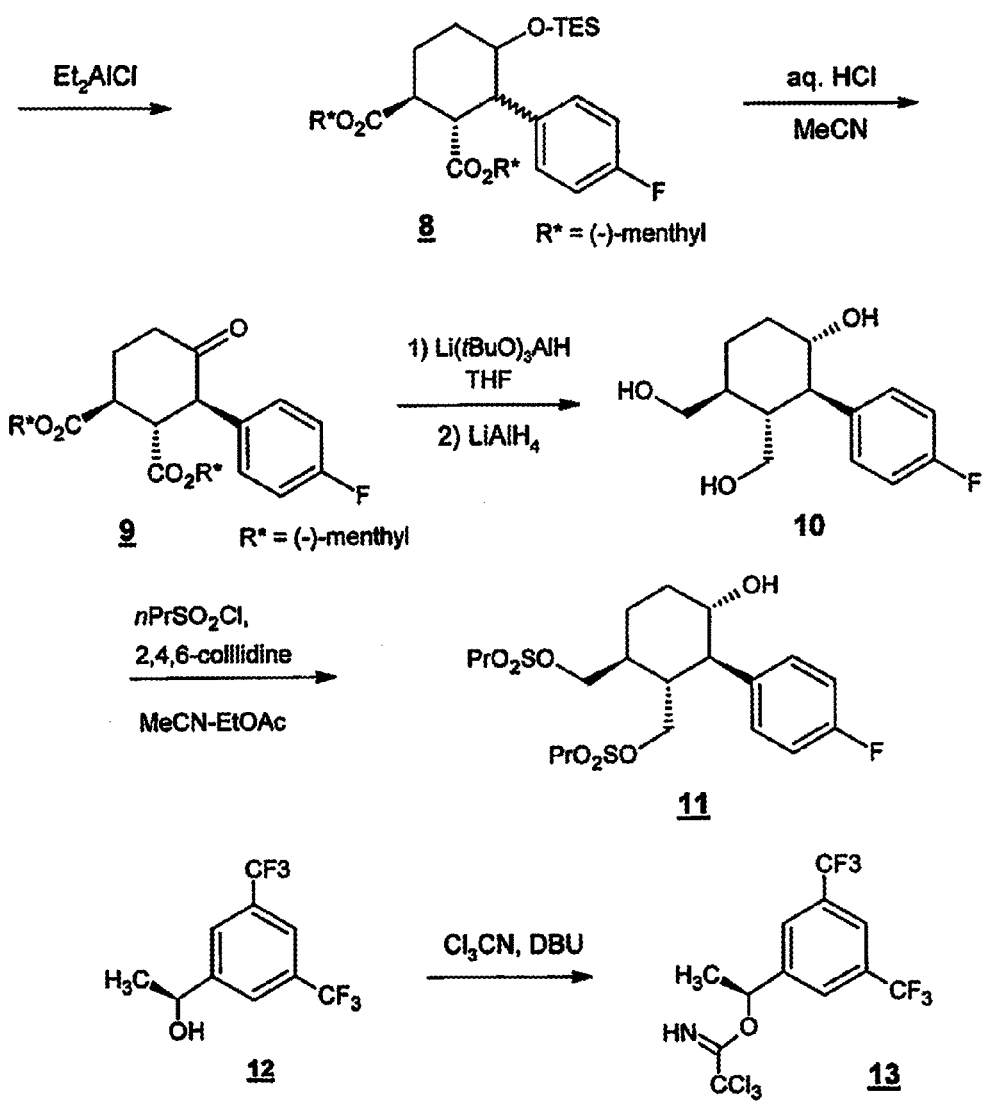
Figure 1:
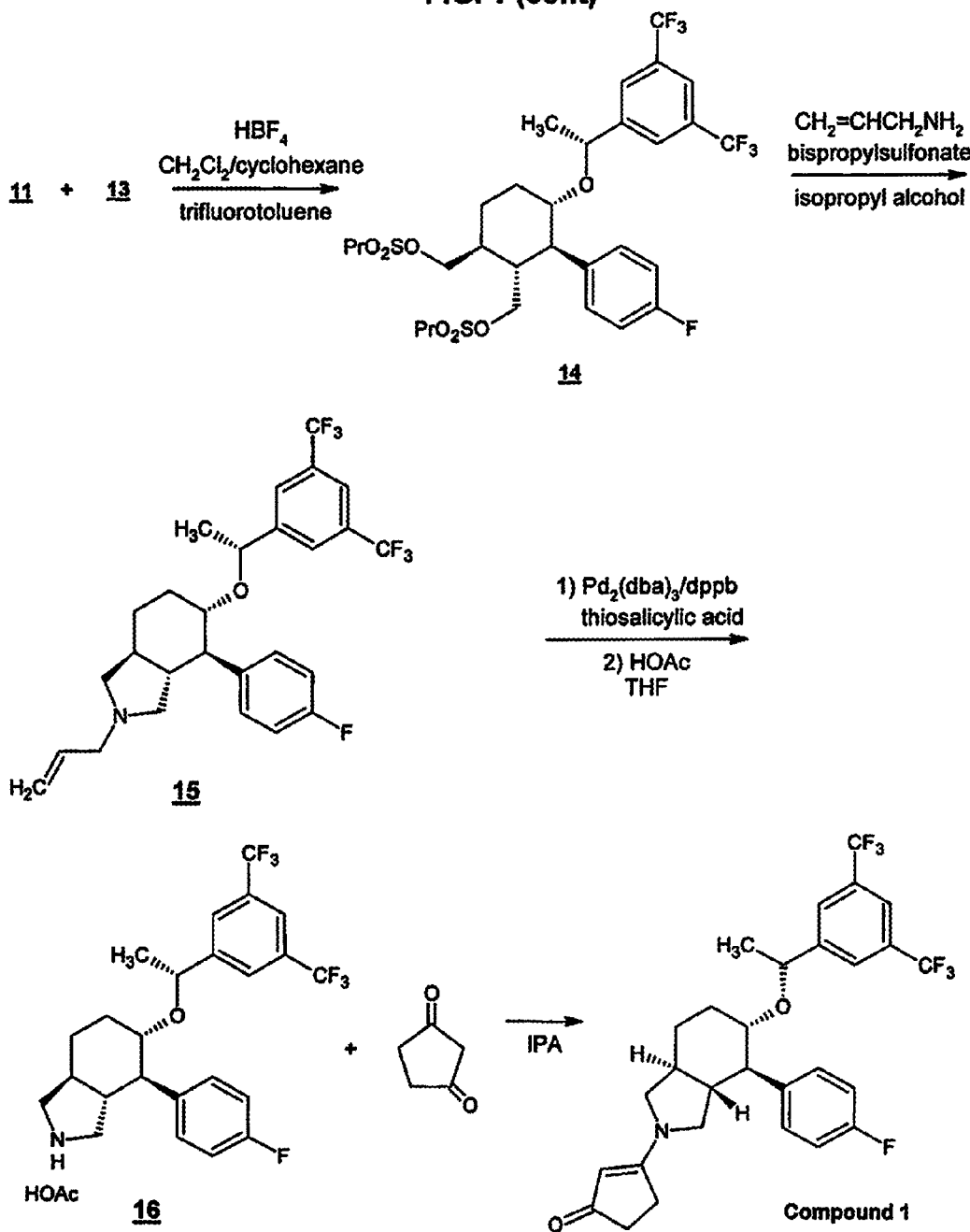

Unless defined otherwise, all technical and scientific terms used herein have the same meaning as commonly understood by one of ordinary skill in the art to which this application belongs. It must be noted that as used herein and in the appended claims, the singular forms "a", "and", and "the" include plural referents unless the context clearly dictates otherwise.

Reference will now be made in detail to certain preferred methods of treatment, compounds and methods of administering these compounds. The invention is not limited to those preferred compounds and methods, but rather is defined by the claim(s) issuing herefrom.

Introduction

Serlopitant is a neurokinin-1 (NK-1) receptor antagonist. The present invention provides a method for treating chronic pruritus and related conditions using serlopitant or a pharmaceutically acceptable salt or hydrate thereof. Chemically, the generic name serlopitant refers to the compound of Compound 1:

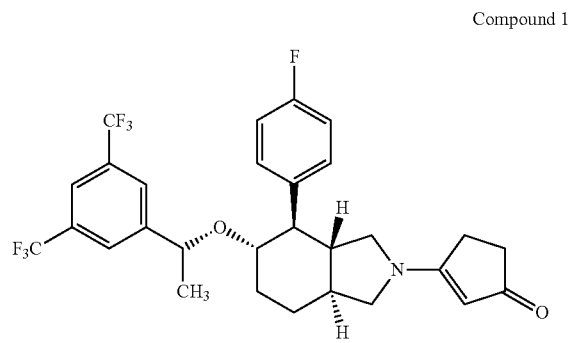

Compound 1

The I.U.P.A.C. name for the compound is 3-[(3aR,4R,5S,7aS)-5-[(1R)-1-[3,5-bis(trifluoromethyl)phenyl]ethoxy]-4-(4-fluorophenyl)-1,3,3a,4,5,6,7,7a-octahydroisoindol-2-yl]cyclopent-2-en-1-one. Alternatively, Compound 1 may be named 3-[(3aR,4R,5S,7aS)-5-{(1R)-1-[3,5-bis(trifluoromethyl)phenyl]ethoxy}-4-(4-fluorophenyl)octahydro-2H-isoindol-2-yl]cyclopent-2-en-1-one. For purposes of the present invention, it is understood that any of these designations for Compound 1 may be interchangeably used and have the same meaning. It is further understood that the invention also encompasses the racemic form of serlopitant (Compound 1).

Serlopitant has previously been disclosed as a neurokinin-1 (NK-1) receptor antagonist, an inhibitor of tachykinin and, in particular, of substance P (J. Jiang, et al., *J. Med. Chem.*, 2009, 52:3039-3046)). Neurokinin receptors are part of the larger family of G-protein coupled receptors that elicit many of their effects via activation of the inositol phosphate signal transduction pathway. NK-1 receptors are present in both the central and peripheral nervous system and in vascular endothelial cells, muscle and cells of the immune system. Compound 1 is unusually selective (>39,000 fold) for the cloned human NK-1 receptor over the cloned human NK-2 and NK-3 receptors, as demonstrated using Chinese hamster ovary cells stably expressing the respective receptors (Jiang et al., 2009). Jiang et al. showed that serlopitant binds to the human NK-1 receptor with a $K_d$ of 46 pM and that it displaces substance P binding at the same receptor with an $IC_{50}$ of 61 pM.

Compound 1 is a weak reversible inhibitor of human CYP-3A4, 2C8, 2C9, 2C19, 2D6, and 1A2 enzymes, the $IC_{50}$ values of which are 39, 58, 30, 29, 35, and >100 µM, respectively. Serlopitant did not significantly induce CYP-3A4 mRNA in three individual preparations of human hepatocytes. These data suggest that serlopitant will have minimal drug-drug interaction liability in humans and that any drug-drug interactions will be reduced in comparison with other NK-1 receptor antagonists. Although broad-based counter-screening of serlopitant in more than 145 assays identified a number of weak activities between 1 and 10 µM, no assays for which $IC_{50} < 1$ µM were observed. Therefore, off-target activities were more than 20000-fold less potent than hNK-1 activity (Jiang et al., 2009).

It has been suggested serlopitant and its analogs would be useful in the prevention and treatment of a variety of clinical conditions characterized by the presence of an excess of tachykinin, in particular substance P, activity. Serlopitant has been disclosed as a treatment for emesis and for urinary incontinence (U.S. Pat. No. 7,217,731, U.S. Pat. No. 7,345,083, U.S. Pat. No. 7,544,815, U.S. Pat. No. 7,645,790, and U.S. Pat. No. 7,893,091, the disclosures of which are herein incorporated by reference; U.S. Published Application Nos. U.S. 2009/0270477, U.S. 2010/0113469, and U.S. 2010/0209496, the disclosures of which are herein incorporated by reference; and PCT Publication WO 2007/146224, the disclosure of which is herein incorporated by reference).

The safety and tolerability of serlopitant have been evaluated in several human clinical trials for the treatment or prevention of with overactive bladder (OAB). In one investigation, a total of 557 patients with OAB were randomized into this double-blind, placebo-controlled and active-controlled (tolterodine), dose-ranging study. Serlopitant at 0.25 and 4 mg daily significantly reduced the number of daily micturitions compared with placebo. There were no drug-related serious adverse experiences and the drug was generally well tolerated. However, serlopitant did not show a dose response relationship with micturition frequency, and did not significantly influence the secondary efficacy end points of urinary urgency, urge incontinence and total incontinence. Tolterodine was numerically more effective than serlopitant at all efficacy end points and statistically significantly more effective than placebo. Serlopitant was not associated with the adverse experience of dry mouth common in patients receiving tolterodine, a muscarinic antagonist. (See: Frenkl, T. L. et al., *J. Urology*, 2009, 181(4), Suppl. S, p. 676; Frenkl, T. L. et al., *Neurourol. Urodyn.*, 2009, 28(2):143-144; Frenkl, T. L. et al., *European Urology Supplements*, 2009, 8(4):134; Frenkl, Tara L, et al., *J. Urology*, 2010, 184(2):616-622.)

Chemical Description of Serlopitant

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, ethanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

The term "solvate" refers to an aggregate that consists of a solute ion or molecule with one or more solvent molecules. "Solvates" include hydrates, that is, aggregates of a compound of interest with water. It will be understood that, as used herein, references to the compounds of the present invention are meant to also include the solvates.

The term "polymorph" refers to a crystalline form of a compound that can crystallize in different forms. The invention also encompasses polymorphs of serlopitant. Examples of polymorphs of serlopitant include without limitation anhydrous crystalline Forms I and II of free base serlopitant as disclosed in U.S. Pat. App. Pub. No. 2009/0270477 to Kuethe et al. Form I is characterized by diffraction peaks obtained from X-ray powder diffraction pattern corresponding to d-spacings of 10.4, 9.9, 9.2, 5.5, 5.0, 4.1, 3.9, 3.6 and 3.5 angstroms. Form II is characterized by diffraction peaks obtained from X-ray powder diffraction pattern corresponding to d-spacings of 7.7, 5.3, 4.9, 4.8, 4.6, 4.2, 3.9, 3.8 and 2.8 angstroms. U.S. 2009/0270477 is incorporated herein by reference in its entirety.

Chemical Synthesis.

Serlopitant may be prepared as described by Jiang et al. (*J. Med. Chem.* 2009, 52:3039-3046), which is herein incorporated by reference in its entirety. Alternatively, the method of Kuethe et al., as described in U.S. Pat. No. 7,544,815, or Bunda et al., as described in U.S. Pat. No. 7,217,731, both of which are herein incorporated by reference in their entirety, may be used.

The method of Kuethe et al. is depicted in FIG. 1. Briefly, commercially available 4-fluorophenylacetic acid (2) (Sigma-Aldrich Co. LLC, St. Louis, Mo.) is reacted with thionyl chloride in DMF/toluene to yield acid chloride (3). The acid chloride (3) is then reacted with the hydrochloride salt of the Weinreb amine ($CH_3NHOCH_3 \cdot HCl$) in the presence of sodium hydroxide to give 2-(4-fluorophenyl)-N-methoxy-N-methylacetamide (4). A vinyl Grignard reaction converts (4) to 1-(4-fluorophenyl)but-3-en-2-one (5). TES dienyl ether (6) is produced from the reaction of (5) with chlorotriethylsilane (TESCI) in the presence of $iPr_2NEt_2$.

Commercially available fumaryl chloride and two equivalents of (−)-menthol (both Sigma-Aldrich) are reacted to yield di-(−)-menthylfumarate (7). A Diels-Alder reaction between (6) and (7) produces (8). Any E-isomer of the diene (<5%) that is present does not react in the Diels-Alder reaction. Deprotection and epimerization of (8) in acid gives (9). The desilylation of (8) initially gave a mixture of 2,3-cis- and 2,3-trans-ketones, which, driven by crystallization of desired (9), isomerized to the predominantly trans compound. Reduction of (9) with lithium tri-t-butoxy aluminum hydride ($Li(t-BuO)_3AlH$), followed by lithium aluminum hydride ($LiAlH_4$), produces triol (10), which is then protected with n-propyl sulfonyl chloride ($nPrSO_2Cl_2$) to give (11).

S-BTBA ((S)-1-[3,5-bis(trifluoromethyl)] phenylethanol)) (12) is reacted with trichloroacetonitrile (Sigma-Aldrich) in the presence of base 1,8-diazabicycloundec-7-ene (DBU) to produce imidate (13). $HBF_4$ is used to catalyze the reaction of (11) with (13) to yield ether (14). Treatment with allylamine and bis-propylsulfonate cyclizes (14) to allylamine-protected pyrrolidine (15). Removal of the allyl protecting group with thiosalicylic acid and 1,4-bis(diphenylphosphino)butane (dppb), followed by bis(dibenzylideneacetone)palladium ($Pd_2(dba)_3$) and isolation with acetic acid gives crystalline (16). Finally, (16) is reacted with 1,3-cyclopentanedione (Sigma-Aldrich) in isopropyl alcohol to give Compound 1. Compound 1 is a white to off-white powder. It is freely soluble in methanol, soluble in ethanol, slightly soluble in isopropyl acetate, sparingly soluble in isopropyl alcohol, ethyl acetate, and acetonitrile, and insoluble in water.

Pharmaceutical Compositions

Compositions containing serlopitant or a pharmaceutically acceptable salt, solvate or polymorph thereof as the active ingredient may be advantageously used to treat chronic pruritus. While it is possible for serlopitant or a pharmaceutically acceptable salt, solvate or polymorph thereof to be administered alone, it is preferable to present it as a formulation. The compositions, or dosage forms, may be administered or applied singly, or in combination with other agents. The formulations may also deliver serlopitant to a patient in combination with another pharmaceutically active agent.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional pharmaceutically acceptable carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier. Said compositions are prepared according to conventional mixing, granulating, or coating methods, respectively, and contain about 0.1 to 75%, preferably about 1 to 50%, of the active ingredient.

By "pharmaceutically acceptable" it is meant the carrier, diluent or excipient must be compatible with the other ingredients of the formulation and not deleterious to the recipient thereof. Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, cornstarch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastro-intestinal tract and thereby provide a sustained action over a longer period. A tablet may be made by compressing or molding the active ingredient optionally with one or more pharmaceutically acceptable ingredients. Compressed tablets may be prepared by compressing, in a suitable machine, the active ingredient in a free-flowing form such as a powder or granules, optionally mixed with a binder, lubricant, inert diluent, surface active, or dispensing agent. Molded tablets may be made by molding, in a suitable machine, a mixture of the powdered active ingredient and a suitable carrier moistened with an inert liquid diluent.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. In particular, a pharmaceutical composition of the present invention may comprise a liquid-filled capsule dosage form in which the active ingredient is in solution in certain combinations of liquid and semi-solid excipients. In one embodiment, the invention is directed to a solution comprising the active agent 3-[(3aR,4R,5S,7aS)-5-{(1R)-1-[3,5-bis(trifluoromethyl)phenyl]ethoxy}-4-(4-fluorophenyl)-octahydro-2H-isoindol-2-yl]cyclopent-2-en-1-one (Compound 1) or a pharmaceutically acceptable salt, solvate or polymorph thereof, and an amphiphilic agent, said amphiphilic agent being a fatty acid ester of glycerol, propylene glycol or sorbitol, as described in U.S. Published Application No. 2010/0209496 (Dakou et al.), which is herein incorporated by reference in its entirety. Preferably, the amphiphilic agent consists essentially of mono- and di-glycerides of C8 to C12 saturated fatty acids and mixtures thereof.

Compositions for oral administration may also be formulated as aqueous suspensions containing the active ingredient in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives.

The active ingredient of the present invention may be administered in an oral sustained release formulation. "Sustained release" refers to release of an active agent from a dosage form at a rate effective to achieve a therapeutic amount of the agent, or active metabolite thereof, in the systemic blood circulation over a prolonged period of time relative to that achieved by oral administration of a conventional formulation of the agent. Release of the agent occurs over an extended period of hours, for example, over a period of at least 6 hours, over a period of at least 8 hours, over a period of at least 12 hours, or over a period of at least 24 hours.

Suitable topical formulations and dosage forms include ointments, creams, gels, lotions, pastes, and the like, as described in Remington: The Science and Practice of Pharmacy (21$^{st}$ Edition, University of the Sciences in Philadelphia, 2005). Ointments are semi-solid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. Creams are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant. Gels are semisolid, suspension-type systems. Single-phase gels contain organic macromolecules (polymers) distributed substantially uniformly throughout the carrier liquid, which is typically aqueous, but also, preferably, contain an alcohol such as ethanol or isopropanol and, optionally, an oil. In order to prepare a uniform gel, dispersing agents such as alcohol or glycerin can be added, or the gelling agent can be dispersed by trituration, mechanical mixing or stirring, or combinations thereof. Lotions are preparations to be applied to the skin surface without friction, and are typically liquid or semiliquid preparations in which solid particles, including the active agent, are present in a water or alcohol base. Lotions are usually suspensions of finely divided solids and will typically contain suspending agents to produce better dispersions as well as compounds useful for localizing and holding the active agent in contact with the skin. Pastes are semisolid dosage forms in which the active agent is suspended in a suitable base. Depending on the nature of the base, pastes are divided between fatty pastes or those made from single-phase aqueous gels.

Various additives, known to those skilled in the art, may be included in the topical formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. For those drugs having an unusually low rate of permeation through the skin or mucosal tissue, it may be desirable to include a permeation enhancer in the formulation. The formulation may also contain irritation-mitigating additives to minimize or eliminate the possibility of skin irritation or skin damage resulting from the drug, the enhancer, or other components of the dosage form. The formulations may also contain ether physiologically acceptable excipients or other minor additives, such as fragrances, dyes, emulsifiers, buffers, cooling agents (e.g. menthol), antibiotics, stabilizers or the like. In some instances, one component may serve more than one function.

The concentration of the active agent in a topical formulation can vary a great deal, and will depend on a variety of factors, including the disease or condition to be treated, the nature and activity of the active agent, the desired effect, possible adverse reactions, the ability and speed of the active agent to reach its intended target, and other factors within the particular knowledge of the patient and physician. The formulations will typically contain on the order of about 0.1 wt % to 50 wt % active agent, preferably about 0.1 wt % to 5 wt % active agent, optimally about 5 wt % to 20 wt % active agent.

In some embodiments, a topical dosage form of serlopitant is formulated as a buccal or sublingual tablet or pill. Advantages of a buccal or sublingual tablet or pill include avoidance of first-pass metabolism and circumvention of gastrointestinal absorption. In addition to a therapeutically effective amount of serlopitant, the buccal or sublingual tablet or pill can contain suitable excipients, including without limitation any combination of fillers and diluents (e.g., mannitol and sorbitol), binding agents (e.g., sodium carbonate), wetting agents (e.g., sodium carbonate), disintegrants (e.g., crospovidone and croscarmellose sodium), lubricants (e.g., silicon dioxide [including colloidal silicon dioxide] and sodium stearyl fumarate), stabilizers (e.g., sodium bicarbonate), flavoring agents (e.g., spearmint flavor), sweetening agents (e.g., sucralose), and coloring agents (e.g., yellow iron oxide). The buccal or sublingual tablet or pill containing serlopitant can be used to treat, e.g., any pruritus-associated condition described herein.

The pharmaceutical compositions of the present invention may be formulated as a depot formulation for administration via intramuscular or subcutaneous injection. Depot formulations are efficient, well-tolerated, sustained or delayed release compositions of the active ingredient that are therapeutically effective for a number of weeks, such as at least one week, at least two weeks, at least three weeks, at least four weeks, at least five weeks, or at least six weeks or more. In addition to the active agent, additional ingredients may be used in the depot formulations of the present invention including surfactants, solubilizers, emulsifiers, preservatives, isotonicity agents, dispersing agents, wetting agents, fillers, solvents, buffers, stabilizers, lubricants, and thickening agents. A combination of additional ingredients may also be used. The amount of the active ingredient in a depot formulation will depend upon the severity of the pruritus being treated.

The compositions of the present invention may be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration. These examples of unit dosage forms is not intended to be limiting in any way, but merely to represent typical examples in the pharmacy arts of unit dosage forms.

The compositions of the present invention may also be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

Topical Compositions Comprising Serlopitant

Topical formulations for application to the skin or mucosa can be useful for treatment of conditions of the upper skin or mucosal layers and for transdermal or transmucosal administration of an active agent to the local tissue underlying the skin or mucosa and, if desired, into the blood for systemic distribution. Advantages of topical administration can include avoidance of first-pass metabolism, circumvention of gastrointestinal absorption, delivery of an active agent with a relatively short biological half-life, more controlled release of the active agent, administration of a more uniform plasma dosing of the active agent, and improvement in user compliance.

In general and in addition to the disclosure on topical formulations described elsewhere herein, compositions suitable for topical administration include without limitation liquid or semi-liquid preparations such as sprays, gels, liniments, lotions, oil-in-water or water-in-oil emulsions such as creams, foams, ointments and pastes, and solutions or suspensions such as drops (e.g., eye drops, nose drops and ear drops). In some embodiments, a topical composition comprises an active agent dissolved, dispersed or suspended in a carrier. The carrier can be in the form of, e.g., a solution, a suspension, an emulsion, an ointment or a gel base, and can contain, e.g., petrolatum, lanolin, a wax (e.g., bee wax), mineral oil, a long-chain alcohol, polyethylene glycol or polypropylene glycol, a diluent (e.g., water and/or an alcohol [e.g., ethanol or propylene glycol]), an emulsifier, a stabilizer or a thickening agent, or a combination thereof. A topical composition can include, or a topical formulation can be administered by means of, e.g., a transdermal patch, a microneedle patch or an iontophoresis device. A transdermal patch can contain, e.g., a microporous membrane made of a suitable material (e.g., cellulose nitrate or acetate, propylene or a polycarbonate), a skin adhesive and backing material. A topical composition can deliver the active agent transdermally (including percutaneously and transmucosally) via a concentration gradient or an active mechanism (e.g., ionospheres).

Representative kinds of topical compositions are described below for purposes of illustration.

I. Topical Compositions Comprising a Permeation Enhancer

In some embodiments, a topical composition comprises serlopitant and a permeation enhancer. The composition can optionally contain an additional therapeutic agent. In certain embodiments, the composition contains serlopitant in free base form.

The permeation enhancer increases the permeability of the skin or mucosa to the therapeutic agent(s). In certain embodiments, the permeation enhancer is N-lauroyl sarcosine, sodium octyl sulfate, methyl laurate, isopropyl myristate, oleic acid, glyceryl oleate or sodium lauryl sulfoacetate, or a combination thereof. In certain embodiments, the composition contains on a weight/volume (w/v) basis the permeation enhancer in an amount of about 1-20%, 1-15%, 1-10% or 1-5%. To enhance further the ability of the therapeutic agent(s) to penetrate the skin or mucosa, the composition can also contain a surfactant, an azone-like compound, an alcohol, a fatty acid or ester, or an aliphatic thiol.

The composition can further contain one or more additional excipients. Suitable excipients include without limitation solubilizers (e.g., $C_2$-$C_6$ alcohols), moisturizers or humectants (e.g., glycerol [glycerin], propylene glycol, amino acids and derivatives thereof, polyamino acids and derivatives thereof, and pyrrolidone carboxylic acids and salts and derivatives thereof), surfactants (e.g., sodium laureth sulfate and sorbitan monolaurate), emulsifiers (e.g., cetyl alcohol and stearyl alcohol), thickeners (e.g., methyl cellulose, ethyl cellulose, hydroxymethyl cellulose, hydroxypropyl cellulose, polyvinylpyrrolidone, polyvinyl alcohol and acrylic polymers), and formulation bases or carriers (e.g., polyethylene glycol as an ointment base). As a non-limiting example, the base or carrier of the composition can contain ethanol, propylene glycol and polyethylene glycol (e.g., PEG 300), and optionally an aqueous liquid (e.g., isotonic phosphate-buffered saline).

The topical composition can have any suitable dosage form, such as a solution (e.g., eye drop, nose drop or ear drop), a suspension, an emulsion, a cream, a lotion, a gel, an ointment, a paste, a jelly, a foam, a shampoo, or a spray. In some embodiments, the composition is applied to the skin or mucosa covering a surface area of about 10-800 cm², 10-400 cm² or 10-200 cm². The composition can deliver the therapeutic agent(s) to the skin or mucosa or the underlying tissue. The composition can also be formulated for transdermal administration of the therapeutic agent(s) to the systemic circulation, e.g., as a transdermal patch or a microneedle patch.

II. Topical Compositions Comprising a Permeation Enhancer and a Volatile Liquid

In further embodiments, a topical composition comprises serlopitant, a permeation enhancer and a volatile liquid. The composition can optionally contain an additional therapeutic agent. In certain embodiments, the composition contains serlopitant in free base form.

The permeation enhancer increases the permeability of the skin or mucosa to the therapeutic agent(s). In some embodiments, the permeation enhancer is selected from the group consisting of $C_8$-$C_{18}$ alkyl aminobenzoates (e.g., $C_8$-$C_{18}$ alkyl p-aminobenzoates), $C_8$-$C_{18}$ alkyl dimethylaminobenzoates (e.g., $C_8$-$C_{18}$ alkyl p-dimethylaminobenzoates), $C_8$-$C_{18}$ alkyl cinnamates, $C_8$-$C_{18}$ alkyl methoxycinnamates (e.g., $C_8$-$C_{18}$ alkyl p-methoxycinnamates), and $C_8$-$C_{18}$ alkyl salicylates. In certain embodiments, the permeation enhancer is octyl salicylate, octyl p-dimethylaminobenzoate or octyl p-methoxycinnamate, or a combination thereof.

The volatile liquid can be any volatile, skin- or mucosa-tolerant solvent. In certain embodiments, the volatile liquid is a $C_2$-$C_5$ alcohol or an aqueous solution thereof, such as ethanol or isopropanol or an aqueous solution thereof. An aerosol propellant (e.g., dimethyl ether) can be considered as a volatile liquid. In some embodiments, the volatile liquid functions as a carrier or vehicle of the composition.

The composition can optionally contain a thickening agent. Non-limiting examples of thickening agents include cellulosic thickening agents (e.g., ethyl cellulose, hydroxypropyl cellulose and hydroxypropyl methylcellulose), povidone, polyacrylic acids/polyacrylates (e.g., Carbopol® polymers), Sepigel® (polyacrylamide/isoparaffin/laureth-7), and the Gantrez® series of polymethyl vinyl ether/maleic anhydride copolymers (e.g., butyl ester of PMV/MA copolymer Gantrez® A-425).

In some embodiments, the composition contains on a weight basis about 0.5-10%, 0.5-5% or 1-5% of serlopitant, about 1-20%, 1-15% or 1-10% of the permeation enhancer, and about 40-98%, 45-95%, 50-90% or 60-80% of the volatile liquid. In further embodiments, the composition optionally contains on a weight basis about 1-40%, 1-30%, 1-20% or 5-20% water and/or about 0.1-15%, 0.5-10% or 1-5% of a thickening agent.

For purposes of illustration, in certain embodiments a topical spray composition contains about 0.5-5% w/v of serlopitant, about 2-10% w/v of octyl salicylate or octyl p-methyoxycinnamate, and about 95% aqueous ethanol as the carrier. In further embodiments, a topic gel composition comprises about 0.5-5% w/v of serlopitant, about 1-10% w/v of octyl salicylate or octyl p-methyoxycinnamate, about 0.5-5% w/v of a Carbopol® polyacrylic acid, and about 70% aqueous ethanol as the carrier, and optionally about 1-10% w/v of a basic solution (e.g., 0.1 N NaOH). In additional embodiments, a topical lotion composition contains about 0.5-5% w/v of serlopitant, about 1-10% w/v of octyl salicylate or octyl p-methyoxycinnamate, about 1-5% w/v of ethyl cellulose or hydroxypropyl cellulose, and about 90% aqueous ethanol as the carrier.

The composition can further comprise other excipients, such as a compounding agent (e.g., paraffin oil, silicone oil, a vegetable oil, or a fatty ester such as isopropyl myristate), a diluent, a co-solvent (e.g., acetone or a glycol ether such as diethylene glycol monoethyl ether), an emulsifier, a surfactant (e.g., an ethoxylated fatty alcohol, glycerol mono stearate or a phosphate ester), a stabiliser, an antioxidant or a preservative (e.g., a hydroxybenzoate ester), or a combination thereof. For example, a co-solvent and/or a surfactant can be used to maintain the therapeutic agent(s) in solution or suspension at the desired concentration.

The topical composition can have any suitable dosage form, such as a cream, a lotion, a gel, an ointment, a mousse, a spray or aerosol, or any transdermal device (e.g., a patch) that administers a drug by absorption through the skin or mucosa. In some embodiments, the topical composition is applied to the skin or mucosa covering a surface area of about 10-800 cm², 10-400 cm² or 10-200 cm².

III. Topical Compositions Comprising a Permeation Enhancer and Another Excipient In yet further embodiments, a topical composition comprises serlopitant, a permeation enhancer, and at least one of a lipophilic solvent, a formulation base and a thickener. In some embodiments, the composition contains a lipophilic solvent and a formulation base, or the same substance can function as both a lipophilic solvent and a formulation base. In further embodiments, the composition contains a lipophilic solvent, a formulation base and a thickener. The composition can optionally comprise an additional therapeutic agent. In certain embodiments, the composition contains serlopitant in free base form.

The permeation enhancer increases the permeability of the skin or mucosa to the therapeutic agent(s). Non-limiting examples of permeation enhancers include dimethyl sulfoxide (DMSO), decylmethylsulfoxide, laurocapram, pyrrolidones (e.g., 2-pyrrolidone and N-methyl-2-pyrrolidine), surfactants, alcohols (e.g., oleyl alcohol), polyethylene glycol (e.g., PEG 400), diethylene glycol monoethyl ether, oleic acid, and fatty acid esters (e.g., isopropyl myristate, methyl laurate, glycerol monooleate, and propylene glycol monooleate).

Non-limiting examples of liphophilic solvents include lipophilic alcohols (e.g., hexylene glycol, octyldodecanol, oleyl alcohol and stearyl alcohol), polyethylene glycol (e.g., PEG 100, PEG 300, PEG 400 and PEG 3350), diethylene glycol monoethyl ether, polysorbates (e.g., Tween® 20 to 80), Labrasol®, fatty acid esters (e.g., isopropyl myristate and diisopropyl adipate), diethyl sebacate, propylene glycol monocaprylate, propylene glycol laurate, mono- and diglycerides (e.g., Capmul® MCM), medium-chain triglycerides, caprylic/capric triglyceride, glyceryl monocaprylate, glyceryl monooleate, glyceryl mono-linoleate, glycerol oleate/propylene glycol, mineral oil, and vegetable oils.

A liphophilic solvent may also function as a formulation base or carrier. For example, polyethylene glycol (e.g., from PEG 100 to PEG 3500, such as PEG 300, PEG 400 and PEG 3350) can function as a liphophilic solvent and a formulation base.

The composition can also contain a hydrophilic solvent, such as a $C_1$-$C_5$ alcohol (e.g., ethanol, isopropanol, glycerol, propylene glycol and 1,2-pentanediol) and/or water.

The composition can contain a thickener to increase the viscosity and/or the physical stability of the composition. Examples of thickeners include without limitation glycerol, stearyl alcohol, and polymers (e.g., polydimethylsiloxane [dimethicone] and Carbopol® polymers).

In some embodiments, the composition further contains an antioxidant. Non-limiting examples of antioxidants include butylated hydroxyanisole (BHA), butylated hydroxytoluene (BHT), tocopherols (e.g., Vitamin E and esters thereof), flavinoids, glutathione, ascorbic acid and esters thereof, DMSO, and chelating agents (e.g., EDTA and citric acid).

In certain embodiments, the topical composition comprises on a w/w basis about 0.5-10% or 1-5% of serlopitant, about 2-30% or 5-20% of a permeation enhancer, about 20-80% or 30-70% of a lipophilic solvent that may also function as a formulation base, about 0.1-10% or 1-7.5% of a thickener, and about 0.01-2% or 0.05-1% of an antioxidant. As a non-limiting example, a topical composition can contain serlopitant, PEG 400 and/or PEG 3350 as lipophilic solvent(s) and formulation base(s), diethylene glycol monoethyl ether, oleyl alcohol and/or isopropyl myristate as permeation enhancer(s), stearyl alcohol as a thickener, and BHT as an antioxidant.

The topical composition can have any suitable dosage form, such as a cream, a lotion, a gel, an ointment, a jelly, a paste, or any transdermal device (e.g., a patch) that administers a drug by absorption through the skin or mucosa.

IV. Topical Compositions Comprising a Permeation Enhancer and an Adhesive

In additional embodiments, a topical composition comprises serlopitant, a permeation enhancer and an adhesive. The composition can optionally contain an additional therapeutic agent. In certain embodiments, the composition contains serlopitant in free base form.

The permeation enhancer increases the permeability of the skin or mucosa to the therapeutic agent(s). The permeation enhancer can be, e.g., a fatty acid ester having a fatty acyl chain length of $C_8$-$C_{20}$ or $C_{12}$-$C_{18}$ and a $C_1$-$C_6$ or $C_2$-$C_4$ alcohol component (e.g., isopropanol). In certain embodiments, the permeation enhancer is isopropyl myristate or isopropyl palmitate. In some embodiments, the permeation enhancer is in an amount of about 0.1-20%, 0.5-15%, 1-15%, 2-12% or 4-10% by weight of the composition or the skin-contacting layer of a transdermal patch.

The adhesive maintains contact of the topical composition to the skin or mucosa. Non-limiting examples of adhesives include acrylics/acrylates (e.g., polyacrylates, including polyalkyl acrylates and Duro-Tak® polyacrylates), polyvinyl acetate, ethylenevinylacetate copolymers, polysiloxanes, polyurethanes, plasticized polyether block amide copolymers, natural and synthetic rubbers, plasticized styrene-butadiene rubber block copolymers (e.g., Duro-Tak® 87-6173), and mixtures thereof.

The topical composition can comprise one or more additional excipients. The additional excipient(s) can be, e.g., a diluent, an emollient, a plasticizer, or an agent that reduces irritation to the skin or mucosa, or a combination thereof.

In certain embodiments, the topical composition prior to application to the skin or mucosa is substantially free of water, tetraglycol (glycofurol) and/or a hydrophilic organic solvent (e.g., a $C_1$-$C_5$ alcohol).

The composition can administer the therapeutic agent(s) transdermally (including percutaneously and transmucosally) through a body surface or membrane such as intact unbroken skin or intact unbroken mucosal tissue into the systemic circulation.

In some embodiments, the topical composition is in the form of a transdermal patch for application to the skin or mucosa. The patch has a skin- or mucosa-contacting layer ("skin-contacting layer" for simplicity) laminated or otherwise attached to a support layer. The skin-contacting layer can be covered by a removable release liner before use to protect the skin-contacting surface and to keep it clean until it is applied to the skin or mucosa.

The support layer of the patch acts as a support for the skin-contacting layer and as a barrier that prevents loss of the therapeutic agent(s) in the skin-contacting layer to the environment. The material of the support layer is compatible with the therapeutic agent(s), the permeation enhancer and the adhesive, and is minimally permeable to the components of the patch. The support layer can be opaque to protect the components of the patch from degradation via exposure to ultraviolet light. The support layer is also capable of binding to and supporting the adhesive layer, yet is sufficiently pliable to accommodate the movements of the subject using the patch. The material of the support layer can be, e.g., a metal foil, a metalized polyfoil, or a composite foil or film containing a polymer (e.g., a polyester [such as polyester terephthalate] or aluminized polyester, polyethylene, polypropylene, polytetrafluoroethylene, a polyethylene methyl methacrylate block copolymer, a polyether block amide copolymer, a polyurethane, polyvinylidene chloride, nylon, a silicone elastomer, rubber-based polyisobutylene, styrene, or a styrene-butadiene or styrene-isoprene copolymer). The release liner can be made of the same material as the support layer, or can be a film coated with an appropriate release surface.

Pruritus

Pruritus is a physiological perception within the sensory neuronal network in the skin which, along with pain and physical or mechanical stimuli, can serve as a warning system against potential bodily threats. Itching is an unpleasant sensation that can lead to scratching, but is independent of pain. The International Federation for the Study of Itch (IFSI) defines chronic pruritus (as opposed to acute pruritus) as itching that lasting six weeks or longer (S. Ständer et al., *Acta Derm. Venereol.*, 2007, 87(4):291-4). Several factors in and on the skin can activate the sensory nerve fibers or modulate their activity and thus trigger, suppress, or exacerbate itching. Physical stimuli such as cold and heat modulate the perception of itching; painful heat and cold can significantly diminish it, while moderate cold intensifies it (Valet et al., *J. Invest. Dermatol.*, 2008, 128 (2):426-33.). Mechanical factors such as rubbing or scratching the skin can briefly suppress itching by activating nerve fibers that selectively activate and de-activate certain areas of the brain (Yosipovitch et al., *J. Invest. Dermatol.*, 2008, 128(7):1806-11).

Chronic pruritus can seriously diminish the quality of life in its sufferers as it can be intractable and incapacitating. It is a seriously debilitating condition, comparable to chronic pain, which can lead to frustration, desperation and depression. Moreover, chronic scratching often produces open skin lesions, subject to primary or secondary infection, scarring and potential disfigurement. Chronic pruritus is often an indication of underlying disease and is always present in diseases such as urticaria and atopic dermatitis. Diagnosis of the underlying disease is desirable and clinical presentation, patient history, and patient self-evaluation form important parts of such diagnosis.

According to Arbeitsgemeinschaft der Wissenschaftlichen Medizinischen Fachgesellschaften (AWMF) (Association of the Scientific Medical Societies of Germany) guidelines, diseases and disorders with chronic pruritus as a symptom may be classified by whether the skin is inflamed or not inflamed (S. Ständer, *Clin. Exp. Dermatol.*, 2006, 31(6):762-7). The IFSI further characterizes pruritus as dermatologic, systemic, neurogenic, psychogenic, mixed and other. Chronic pruritus on non-inflamed skin may result from dermatological diseases, including atopic diathesis, asteatosis, porphyria, suburticarial stages of solar injury, cholinergic, adrenergic urticaria, initial stage of mastocytosis, bullous pemphigoid, and Duhring's disease (dermatitis herpetiformis); from endocrine and metabolic disorders, such as chronic renal insufficiency and the dialysis needed treat it, hepatopathies with cholestasis, diabetes mellitus, malabsorption disorders, anorexia, gluten-enteropathies, hyperthyroidism, hypothyroidism, hyperparathyroidism, and perimenopausal pruritus; from infections including HIV infection, parasites, *Helicobacter pylori*, and helminth-related; from hemotological and lymphoproliferative diseases such as iron deficiency, polycythaemica vera, hypereosinophilia syndrome, myelodysplastic syndrome, Hodgkin's disease, non-Hodgkin's lymphoma, plasmocytoma, and systemic mastocytosis; from solid malignant tumors including cervical, breast, prostate or large intestinal cancer, and carcinoid tumors; from neurological disorders such as brachioradial pruritus, notalgia paraesthetica, post-zoster neuralgia, vulvodynia, neuropathies of various origin, multiple sclerosis, tumors, abscesses, underperfusion, infarctions involving the CNS/spinal cord; from psychogenic disorders such as depression, schizophrenia, and tactile hallucinations; and from intrahepatic cholestasis in pregnant women (pruritus gravidarum).

Chronic pruritus on inflamed skin may be observed in patients with inflammatory skin disease including, but not limited to, atopic dermatitis, allergic, irritant contact dermatitis, exsiccation dermatitis, nummular and dyshidrotic dermatitis, lichen planus, lichen sclerosus et atrophicus, polymorphous light eruption psoriasis, Grover's disease, mucinosis, mastocytosis, and urticaria; infectious skin diseases such as mycoses, bacterial and viral infections, scabies, pediculosis, insect bites, and folliculitides; autoimmune skin diseases including Bullous skin disorders, especially dermatitis herpetiformis (Duhring's disease), and bullous pemphigoid; genodermatoses such as Darier's disease, and Hailey-Hailey disease; pregnancy-related skin diseases including polymorphic eruption of pregnancy (PEP, formerly known as PUPPP), atopic eruption of pregnancy, and pemphigoid gestationis; and neoplasias such as cutaneous T-cell lymphoma (especially the erythrodermic form).

Prurigo nodularis (PN), or nodular prurigo, is a particularly severe form of chronic itching that may treated by methods and compositions of the present invention. Characterized by itchy, excoriated, lichenified papules and nodules, PN can occur at any age, but most often presents in middle-aged and elderly patients on their arms and legs (E. Weisshaar and S. Ständer, *Acta Derm. Venereol.*, 2012, 92:532-533). The etiology of PN is unknown, but it usually occurs in patients with a personal or family history of atopic dermatitis, and often with concomitant medical conditions such as hepatic or renal function, local trauma or insult to the skin, infection, and HIV or other immunodeficiencies. PN may result in permanent changes to the skin, including nodular lichenification, hyperkeratosis, hyperpigmentation, and skin thickening.

Combination Therapies with Serlopitant and Other Antipruritic Agents

Serlopitant, alone or in combination with one or more additional antipruritic agents, can be used to treat pruritus (including acute and chronic pruritus) associated with any condition. The itch sensation can originate, e.g., in the peripheral nervous system (e.g., dermal or neuropathic itch) or in the central nervous system (e.g., neuropathic, neurogenic or psychogenic itch).

Examples of pruritus-associated conditions include without limitation those described elsewhere herein and the following:

dermatological disorders and conditions (including inflammatory and non-inflammatory skin conditions), including but not limited to adult blaschkitis, amyloidoses (e.g., primary cutaneous amyloidosis [including macular amyloidosis, lichen amyloidosis and nodular amyloidosis]), burns (e.g., chemical burns and sunburn), dermatitis {e.g., atopic dermatitis, contact dermatitis (including allergic contact dermatitis, irritant contact dermatitis and photodermatitis), eczema (e.g., autosensitization dermatitis, dermatitis herpetiformis [Duhring's disease], discoid eczema, dyshidrosis [pompholyx], hand eczema, id reaction [generalized eczema], nummular eczema, stasis dermatitis [gravitational eczema], venous eczema and xerotic eczema), pustular dermatitis (e.g., eosinophilic pustular folliculitis [Ofuji's disease], reactive arthritis [Reiter's disease] and subcorneal pustular dermatosis [Sneddon-Wilkinson disease]), and seborrheic dermatitis (e.g., infantile seborrheic dermatitis, Leiner's disease and pityriasis simplex capillitii [dandruff])}, erythroderma (exfoliative dermatitis), folliculitis, pseudofolliculitis barbae (barber's itch), hidradenitis suppurativa, ichthyoses (e.g., ichthyosis vulgaris, congenital ichthyosis, epidermolytic hyperkeratosis and lamellar ichthyosis), lichen planus (e.g., cutaneous lichen planus and oral lichen planus), lichen sclerosis (e.g., lichen sclerosis et atrophicus of the vulva), lichen simplex (e.g., lichen simplex chronicus [neurodermatitis]), linear IgA bullous dermatosis (linear IgA dermatosis), lupus erythematosus (e.g., cutaneous lupus erythematosus, discoid lupus erythematosus and systemic lupus erythematosus), miliaria (sweat rash), palmoplantar keratoderma (e.g., punctate palmoplantar keratoderma), pityriasis (e.g., pityriasis amiantacea, pityriasis lichenoides [including pityriasis lichenoides chronica and pityriasis lichenoides et varioliformis acuta], pityriasis rosea, pityriasis rubra pilaris [Devergie's disease] and pityriasis versicolor), prurigo (e.g., actinic prurigo, Besnier's prurigo, prurigo nodularis, prurigo pigmentosa and prurigo simplex), pruritus ani, pruritus scroti, pruritus vulvae, psoriasis (e.g., erythrodermic psoriasis, Guttate psoriasis [eruptive psoriasis], psoriasis vulgaris [chronic stationary psoriasis], pustular psoriasis, and pustulosis palmaris et plantaris), parapsoriasis (e.g., large plaque parapsoriasis and small plaque parapsoriasis [chronic superficial dermatitis]), puncta pruritica (itchy points), rashes (e.g., intertrigo and perioral dermatitis), rosacea, urticaria (e.g., contact urticaria [including hives] and idiopathic urticaria), vitiligo, xerosis (dry skin), chapped skin (e.g., chapped feet), scalp pruritus, scab healing, scar development, and development of moles, pimples and ingrown hair;

medical disorders and conditions (including peripheral and systemic disorders), including but not limited to atopic diathesis, autoimmune disorders (e.g., celiac disease, dermatomyositis, Graves' disease, pemphigoid [e.g., bullous pemphigoid], scleroderma and Sjögren's syndrome), blood disorders (e.g., anemia [e.g., iron deficiency anemia and sickle cell anemia], hypercalcemia, myelodysplastic syndromes and polycythemia [e.g., polycythemia vera]), Creutzfeldt-Jakob disease (e.g., prion pruritus), diabetes mellitus, genetic diseases (e.g., Alagille syndrome, Darier's disease, epidermolysis bullosa, Hailey-Hailey disease and Sjögren-Larsson syndrome), Grover's disease, HIV/AIDS, kidney disorders (e.g., diabetic nephropathy, glomerulonephritis, chronic kidney disease, end-stage kidney disease and chronic kidney failure), uraemia (e.g., uremic pruritus [renal pruritus]), liver diseases (e.g., cirrhosis [e.g., primary biliary cirrhosis], hepatitis [including hepatitis A, B, C, D and E and their chronic conditions], and liver failure), cholestasis (e.g., cholestatic pruritus), jaundice (e.g., biliary pruritus), lymphadenopathy (e.g., enlarged lymph nodes), mast cell diseases (e.g., mast cell activation syndrome and mastocytosis), multiple sclerosis, neuropathies (e.g., peripheral neuropathy [e.g., brachioradial pruritus, notalgia paresthetica, polyneuropathy and small fiber peripheral neuropathy]), nerve irritation, pinched nerves, parathyroid disorders (e.g., hyperparathyroidism and hypoparathyroidism), thyroid disorders (e.g., hyperthyroidism, hypothyroidism and myxedema), stroke, cancers {e.g., carcinoid syndrome, leukemia (e.g., leukemia cutis and lymphatic leukemia), lymphomas (e.g., Hodgkin's disease and non-Hodgkin lymphomas [e.g., cutaneous B-cell lymphoma and cutaneous T-cell lymphoma (including mycosis fungoides and Sézary's disease)]), Kaposi's sarcoma, multiple myeloma and skin cancers}, tumors (e.g., brain tumor, plasmacytoma, and solid tumors of the cervix, colon and prostate), paraneoplastic pruritus, psychiatric disorders (e.g., stress, anxiety disorders, delusional parasitosis, depression, obsessive-compulsive disorders [e.g., neurotic excoriation], and tactile hallucinations), aging (e.g., senile pruritus) and changes in hormonal balances associated with aging (e.g., perimenopause and menopause);

infections and infestations, including but not limited to cercarial dermatitis (swimmer's itch), insect bites and stings (e.g., by ants, bees, chiggers, fleas, lice [including body lice, head lice and pubic lice], mites, mosquitos, spiders, ticks and wasps), scabies, bacterial infections (e.g., abscess, dermatitis gangrenosa, ecthyma, erythrasma, impetigo and Lyme disease), fungal infections (e.g., candidiasis, dermatophytosis, tinea corporis [ringworm of the body], tinea cruris [jock itch] and tinea pedis [athlete's foot]), viral infections {e.g., herpes (including herpes zoster [shingles] and post-herpetic itch), measles, parvovirus infections (e.g., parvovirus B19), varicella (chickenpox) and Yellow fever}, and worm infections {e.g., helminths (e.g., helminthiasis [helminthosis]), hookworms (e.g., cutaneous larva migrans), *Onchocerca* worms (e.g., onchocerciasis [river blindness]), pinworms, roundworms (e.g., filariasis and trichinosis) and *Schistosoma* worms (e.g., schistosomiasis)};

reactions to allergens and irritants, including but not limited to allergic rhinitis (e.g., pollinosis [including hay fever]), asthma, animal allergens (e.g., cat dander and dog dander), chemical allergens (e.g., acids [e.g., abietic acid and sorbic acid], cosmetics, detergents, dyes, fabric softeners, fungicides, hydroxyethyl starch and latex), food allergens (e.g., milk proteins, peanuts, tree nuts, seafood, spices, preservatives [e.g., nitrates], vitamins [e.g., vitamins A and B], alcohol, caffeine and monosodium glutamate), metal and metal salt allergens (e.g., chromium, cobalt, gold and nickel and salts thereof), plant allergens (e.g., Balsam of Peru and urushiol [e.g., in poison ivy, poison oak and poison sumac]), chemical irritants (e.g., acids, alkalis, metalworking fluids, solvents, surfactants, detergents, soaps, cleaning products, cosmetics, perfumes, deodorants, antiperspirants, food flavorings, spices, preservatives [e.g., formaldehyde and parabens], monomers and polymers [e.g., acrylics, epoxy resins, ethylene oxide, latex and lacquers], and oils [e.g., kerosene]), fabrics (e.g., wool), plant irritants (e.g., alkyl resorcinols [e.g., in *Grevillea banksii*, *Grevillea "Robyn Gordon"* and *Gingko biloba*]), and physical irritants (e.g., water [e.g., aquadynia and aquagenic pruritus), low humidity from air conditioning, and cold temperature);

pruritus caused by drugs/medication, including but not limited to chloroquine, hydroxyethyl cellulose, hydroxyethyl starch, angiotensin-converting enzyme inhibitors, xanthine oxidase inhibitors (e.g., allopurinol), antibiotics (e.g., isoniazid, neomycin, penicillin, sulfonamides and vancomycin), antifungals (e.g., fluconazole, griseofulvin, itraconazole and ketoconazole), neuroleptics/antipsychotics (e.g., phenothiazines), antiarrhythmic drugs (e.g., amiodarone and quinidine), chemotherapeutic drugs, diuretic drugs (e.g., hydrochlorothiazide), statins (e.g., simvastatin), and drugs (e.g., opioids) that activate the histamine $H_1$ receptor or trigger histamine release; and conditions related to pregnancy, including but not limited to gestational pemphigoid, impetigo herpetiformis, intrahepatic cholestasis of pregnancy (pruritus gravidarum), polymorphic eruption of pregnancy, prurigo of pregnancy, pruritic folliculitis of pregnancy, and pruritic urticarial papules and plaques of pregnancy.

One or more additional antipruritic agents can optionally be used in combination with serlopitant to treat pruritus (including acute and chronic pruritus). Examples of antipruritic agents include without limitation:

antihistamines, including but not limited to antihistamines that inhibit action at the histamine $H_1$ receptor (e.g., acrivastine, antazoline, azelastine, bilastine, brompheniramine, buclizine, bromodiphenhydramine, carbinoxamine, cetirizine, chlorpromazine, cyclizine, chlorpheniramine, chlorodiphenhydramine, clemastine, cyproheptadine, desloratadine, dexbrompheniramine, dexchlorpheniramine, dimenhydrinate, dimetindene, diphenhydramine, doxepin, doxylamine, ebastine, embramine, fexofenadine, hydroxyzine, levocetirizine, loratadine, meclozine, mepyramine, mirtazapine, olopatadine, orphenadrine, phenindamine, pheniramine, phenyltoloxamine, promethazine, pyrilamine, quetiapine, rupatadine, tripelennamine and triprolidine), and antihistamines that inhibit action at the histamine $H_4$ receptor (e.g., thioperamide, JNJ 7777120 and VUF-6002), and analogs and derivatives thereof;

serotonin receptor antagonists, including but not limited to 5-$HT_2$ antagonists (e.g., clozapine, cyproheptadine, ketanserin, pizotifen and quetiapine) and 5-$HT_3$ antagonists (e.g., alosetron, cilansetron, dolasetron, granisetron, ondansetron, palonosetron and tropisetron), and analogs and derivatives thereof;

neurokinin-1 (NK-1) receptor antagonists, including but not limited to aprepitant, casopitant (GW679769), dapitant, ezlopitant, fosaprepitant, lanepitant (LY-303870), maropitant, netupitant, nolpitant, orvepitant, rolapitant, vestipitant, vofopitant, AV-818, BIIF 1149CL, CP122,721, DNK-333, GSK-424887, L-733060, L-759274, LY-686017, M516102 and TA-5538, and analogs and derivatives thereof;

opioid receptor antagonists, including but not limited to butorphanol, cyprodime, levallorphan (lorfan or naloxiphan), nalbuphine, nalorphine (lethidrone or nalline), naloxone, naloxol, nalmefene, naltrexone (e.g., naltrexone 1% cream) and naltrexol, and analogs and derivatives thereof;

opioid receptor agonists, including but not limited to selective kappa opioid receptor agonists (e.g., asimadoline, bremazocine, dynorphin, enadoline, ketazocine, nalfurafine, salvinorin A, 2-methoxymethyl salvinorin B, 2-ethoxymethyl salvinorin B, 2-fluoroethoxymethyl salvinorin B, spiradoline, tifluadom, BRL-52537, FE 200665, GR-89696, HZ-2, ICI-199,441, ICI-204,448, LPK-26, U-50488 and U-69,593), and analogs and derivatives thereof;

Janus kinase (JAK) inhibitors, including but not limited to JAK1 inhibitors (e.g., GLPG0634 and GSK2586184), JAK2 inhibitors (e.g., lestaurtinib, pacritinib, CYT387 and TG101348), JAK1/JAK2 inhibitors (e.g., baricitinib and ruxolitinib), and JAK3 inhibitors (e.g., tofacitinib), and analogs and derivatives thereof;

immunomodulators and immunosuppressants, including but not limited to thalidomide, antimetabolites (e.g., antifolates such as methotrexate), and calcineurin inhibitors (e.g., ciclosporin [cyclosporin], pimecrolimus and tacrolimus), and analogs and derivatives thereof;

antidepressants, including but not limited to tricyclic antidepressants (e.g., amitriptyline, amitriptylinoxide, amoxapine, dosulepin [dothiepin], doxepin and melitracen), tetracyclic antidepressants (e.g., amoxapine, maprotiline, mazindol, mianserin, mirtazapine and setiptiline), selective serotonin reuptake inhibitors (SSRIs, e.g., citalopram, dapoxetine, escitalopram, fluoxetine, fluvoxamine, paroxetine and sertraline), and serotonin-norepinephrine reuptake inhibitors (SNRIs, e.g., bicifadine, duloxetine, milnacipran, levomilnacipran, sibutramine, venlafaxine, desvenlafaxine and SEP-227162), and analogs and derivatives thereof;

anticonvulsants, including but not limited to carbamazepine, gabapentin, pregabalin, and valproic acid and salts thereof (e.g., sodium valproate), and analogs and derivatives thereof;

corticosteroids, including but not limited to hydrocortisone types (e.g., cortisone and derivatives thereof [e.g., cortisone acetate], hydrocortisone and derivatives thereof [e.g., hydrocortisone acetate, hydrocortisone-17-aceponate, hydrocortisone-17-buteprate, hydrocortisone-17-butyrate and hydrocortisone-17-valerate], prednisolone, methylprednisolone and derivatives thereof [e.g., methylprednisolone aceponate], prednisone, and tixocortol and derivatives thereof [e.g., tixocortol pivalate]), betamethasone types (e.g., betamethasone and derivatives thereof [e.g., betamethasone dipropionate, betamethasone sodium phosphate and betamethasone valerate], dexamethasone and derivatives thereof [e.g., dexamethasone sodium phosphate], and fluocortolone and derivatives thereof [e.g., fluocortolone caproate and fluocortolone pivalate]), halogenated steroids (e.g., alclometasone and derivatives thereof [e.g., alclometasone dipropionate], beclometasone and derivatives thereof [e.g., beclometasone dipropionate], clobetasol and derivatives thereof [e.g., clobetasol-17-propionate], clobetasone and derivatives thereof [e.g., clobetasone-17-butyrate], desoximetasone and derivatives thereof [e.g., desoximetasone acetate], diflorasone and derivatives thereof [e.g., diflorasone diacetate], diflucortolone and derivatives thereof [e.g., diflucortolone valerate], fluprednidene and derivatives thereof [e.g., fluprednidene acetate], fluticasone and derivatives thereof [e.g., fluticasone propionate], halobetasol [ulobetasol] and derivatives thereof [e.g., halobetasol proprionate], halometasone and derivatives thereof [e.g., halometasone acetate], and mometasone and derivatives thereof [e.g., mometasone furoate]), acetonides and related substances (e.g., amcinonide, budesonide, ciclesonide, desonide, fluocinonide, fluocinolone acetonide, flurandrenolide [flurandrenolone or fludroxycortide], halcinonide, triamcinolone acetonide and triamcinolone alcohol), and carbonates (e.g., prednicarbate), and analogs and derivatives thereof;

local anesthetics, including but not limited to amides (e.g., articaine, bupivacaine, cinchocaine [dibucaine], etidocaine, levobupivacaine, lidocaine [e.g., lidocaine 2.5-5% cream], prilocaine [e.g., prilocaine 2.5% cream], EMLA [lidocaine 2.5%/prilocaine 2.5% cream], mepivacaine, ropivacaine and trimecaine), esters (e.g., benzocaine, chloroprocaine, cocaine, cyclomethycaine, dimethocaine [larocaine], piperocaine, procaine [novocaine], proparacaine, propoxycaine, stovaine and tetracaine [amethocaine]), ethers (e.g., polidocanol [e.g., polidocanol 3% foam] and pramocaine [pramoxine] [e.g., pramoxine 1% cream]), and naturally derived local anesthetics (e.g., cocaine, eugenol, menthol, saxitoxin, neosaxitoxin and tetrodotoxin), and analogs and derivatives thereof;

counterirritants and cooling agents, including but not limited to capsaicin, camphor, mint oil, menthol (e.g., menthol 1-3% cream), and phenol (e.g., in calamine lotion), and analogs and derivatives thereof;

moisturizers, including but not limited to aqueous moisturizers, low pH moisturizers containing an acid (e.g., lactic acid), and moisturizers containing a humectant that attracts and retains water (e.g., glycerol, sorbitol, lactate, urea, and hyaluronic acid and salts thereof), an occlusive that prevents evaporation {e.g., oils (e.g., mineral oil and silicone oil [e.g., dimethicone]) and petroleum jelly (petrolatum)}, and/or an emollient that provides partial hydration and occlusion (e.g., oils, waxes [e.g., lanolin and paraffin], lipids [e.g., phospholipids, ceramides, triglycerides, glycol stearate, glyceryl stearate, fatty acids and squalene], and sterols [e.g., cholesterol and phytosterol]), and analogs and derivatives thereof; and other kinds of antipruritic agents, including but not limited to S-adenosyl methionine, botulinum toxin (e.g., botulinum toxin types A and B), vitamin D and analogs and derivatives thereof (e.g., calcitriol and calcipotriol [calcipotriene]), non-steroidal anti-inflammatory drugs (NSAIDs, e.g., aspirin), cannabinoid receptor agonists (e.g., $CB_2$ agonists, such as palmitoylethanolamide), inhibitors of cytokines (e.g., antibodies to interleukins, such as IL-31), antagonists of the prostaglandin $D_2$ receptor ($DP_1$) and/or the chemoattractant receptor homologous molecule expressed on $TH_2$ cells (CRTH2) (e.g., TS-022), phosphodiesterase (PDE) inhibitors (e.g., PDE4 inhibitors, such as apremilast), protease-activated receptor 2 (PAR2) antagonists (e.g., GB83), transient receptor potential vanilloid (TRPV) antagonists (e.g., TRPV1 antagonists, such as capsazepine and SB-705498), inhibitors of neurotrophic tyrosine kinase receptors (e.g., TrkA inhibitors, such as CT327), antimicrobials (including antibiotics, antifungals, antivirals and antiparasitics, such as crotamiton and rifampin [rifampicin]), bile absorption-reducing or bile sequestering agents (e.g., ursodeoxycholic acid [ursodiol]), ultraviolet radiation (e.g., ultraviolet A and B), and therapeutic agents that treat the underlying causes of the pruritus-associated conditions, and analogs and derivatives thereof.

If desired (e.g., for relief from pruritus during the day), a non-sedating antipruritic agent can be used. For example, second-generation and third-generation antihistamines are designed to be non-sedating, or less sedating than first-generation antihistamines. Non-limiting examples of second-generation and third-generation antihistamines include acrivastine, astemizole, azelastine, bepotastine, bilastine, cetirizine, levocetirizine, ebastine, fexofenadine, ketotifen, levocabastine, loratadine, desloratadine, mizolastine, olopatadine, quifenadine, rupatadine and terfenadine.

In some embodiments, a corticosteroid of moderate or medium potency is used in combination with serlopitant to treat a pruritus-associated condition. Examples of corticosteroids having moderate or medium potency include Groups III, IV and V corticosteroids under the 7-group US classification system and Class II corticosteroids under the 4-class European classification system, including without limitation amcinonide 0.1% (e.g., cream), betamethasone dipropionate 0.05% (e.g., Diprosone® cream/ointment), betamethasone valerate 0.1% (e.g., cream/ointment), clobetasone butyrate 0.05% (e.g., Eumovate® cream), desonide 0.05% (e.g., Tridesilon® cream/ointment and DesOwen® cream/ointment), fluocinolone acetonide 0.01-0.2% (e.g., Synalar® cream/ointment and Synemol® cream), flurandrenolide 0.05% (e.g., Cordran® tape), fluticasone propionate 0.005% (e.g., Cutivate® ointment), fluticasone propionate 0.05% (e.g., Cutivate® cream), halometasone 0.05% (e.g., cream), hydrocortisone butyrate 0.1% (e.g., Locoid® cream/ointment), hydrocortisone valerate 0.2% (e.g., Westcort® cream/ointment), mometasone furoate 0.1% (e.g., Elocon® cream/ointment), triamcinolone acetonide 0.025-0.5% (e.g., Aristocort® cream/ointment, Kenacomb® cream/ointment, Kenalog® cream and Viaderm® KC cream/ointment), and triamcinolone diacetate 0.5% (e.g., cream/ointment).

The optional additional antipruritic agent(s) can be administered to a subject suffering from pruritus concurrently with (e.g., in the same composition as serlopitant or in separate compositions) or sequentially to (before or after) administration of serlopitant. Serlopitant and the optional additional antipruritic agent(s) independently can be administered in any suitable mode, including without limitation orally, topically (e.g., dermally/epicutaneously, transdermally, mucosally, transmucosally, intranasally [e.g., by nasal spray or drop], opthalmically [e.g., by eye drop], pulmonarily [e.g., by inhalation], bucally, sublingually, rectally and vaginally), by injection or infusion (e.g., parenterally, including intramuscularly, subcutaneously, intradermally, intravenously/intravascularly, and intrathecally), and by implantation (e.g., subcutaneously and intramuscularly). In some embodiments, an antipruritic agent is administered topically (e.g., dermally) if the pruritus is localized, and is administered systemically (e.g., orally or intravenously) if the pruritus is widespread (generalized) or has a systemic cause. In certain embodiments, serlopitant and/or the optional additional antipruritic agent(s) are administered orally. In other embodiments, serlopitant and/or the optional additional antipruritic agent(s) are administered topically (e.g., dermally, mucosally, bucally or sublingually).

Serlopitant and the optional additional antipruritic agent(s) independently can be administered in any suitable frequency, including without limitation daily (one, two, three or more times per day), every two days, twice weekly, thrice weekly, weekly, every two weeks, every three weeks, monthly, every two months and every three months. The dosing frequency can depend on, e.g., the mode of administration chosen. For example, a dermal formulation of serlopitant, and/or that of the optional additional antipruritic agent(s), can be applied to the skin of a subject two, three or four times a day. In some embodiments, serlopitant is administered under a chronic dosing regimen. In certain embodiments, serlopitant is administered over a period of at least 2 weeks, 3 weeks, 1 month, 1.5 months, 2 months, 3 months, 4 months, 5 months, 6 months or longer.

Examples of topical dosage forms include without limitation creams, ointments, gels, liniments, lotions, suppositories (e.g., rectal and vaginal suppositories), buccal and sublingual tablets and pills, sprays (e.g., dermal and nasal sprays), and drops (e.g., eye, nose and ear drops). Non-limiting examples of oral dosage forms include solid dosage forms (e.g., cachets, capsules and tablets) and liquid dosage forms (e.g., solutions or suspensions in an aqueous liquid and/or a non-aqueous liquid, and oil-in-water liquid emulsions or water-in-oil liquid emulsions). In a non-limiting example of a formulation for injection, the formulation is in the form of a solution and comprises an antipruritic agent (e.g., a local anesthetic), a vehicle (e.g., a water-based vehicle or sterile water), a buffer, a reducing agent/antioxidant (e.g., sodium metabisulfite if epinephrine is used as a vasoconstrictor) and a preservative (e.g., methylparaben), and optionally a vasoconstrictor (e.g., epinephrine) to increase the duration of the pharmacological effect of the antipruritic agent by constricting the blood vessels, thereby concentrating the antipruritic agent for an extended duration and increasing the maximum dose of the antipruritic agent.

Table 4 provides non-limiting examples of combination therapies employing serlopitant and one or more additional antipruritic agents for the treatment of pruritus associated with various conditions. Table 4 may also show other therapeutic agents used to treat the underlying causes of the conditions.

TABLE 4

| Agents in Addition to Serlopitant | Conditions |
|---|---|
| Corticosteroid | Skin inflammation, chapped skin, atopic dermatitis, contact dermatitis, eczema, seborrheic dermatitis, erythroderma, lichen planus, lichen simplex chronicus, lichen sclerosis, lupus erythematosus, psoriasis, rashes, scabies and burns (e.g., sunburn) |
| Antihistamine (e.g., doxepin for topical use, and sedating diphenhydramine or non-sedating cetirizine for oral use) | Urticaria, allergy-based pruritus, localized pruritus (e.g., insect bites and stings) and generalized pruritus (e.g., chickenpox) |
| Local anesthetic + optional counterirritant/cooling agent | Localized pruritus (e.g., insect bites and stings), and mild to moderate pruritus |
| Counterirritant (e.g., capsaicin) | Chronic localized pruritus (e.g., notalgia paresthetica and prurigo nodularis) |
| Moisturizer &/or calamine | Allergic rashes (e.g., poison ivy/oak and urticaria), burns (e.g., sunburn), and insect bites and stings |
| Moisturizer + optional counterirritant/cooling agent | Atopic dermatitis, contact dermatitis, eczema, seborrheic dermatitis, ichthyosis, psoriasis and xerosis |
| Immunomodulator (e.g., tacrolimus) + optional corticosteroid | Atopic dermatitis |
| JAK inhibitor (e.g., tofacitinib) or PDE inhibitor (e.g., apremilast) or vitamin D (e.g., calcipotriol) | Psoriasis |
| TrkA inhibitor (e.g., CT327) | Atopic dermatitis, psoriasis and cutaneous T-cell lymphoma |
| JAK inhibitor (e.g., ruxolitinib) | Anemia, peripheral neuropathy and polycythemia vera |
| Aspirin (topical) | Lichen simplex chronicus |
| Tricyclic antidepressant (e.g., doxepin) | Chronic severe pruritus |
| Opioid receptor antagonist (e.g., naloxone) | Intractable pruritus of renal and cholestatic diseases |
| 1) Ultraviolet B phototherapy + erythropoietin; or 2) Cholestyramine + opioid receptor antagonist (e.g., naltrexone) + activated charcoal; or 3) Thalidomide | Chronic renal disease |
| 1) Ion-exchange resin (e.g., cholestyramine) + opioid receptor antagonist (e.g., naloxone); or 2) SSRI, S-adenosyl methionine, rifampicin &/or ursodeoxycholic acid; or 3) Cholestyramine + opioid receptor antagonist (e.g., nalmefene) + serotonin antagonist (e.g., ondansetron) + ursodeoxycholic acid + rifampicin + optional bright-light therapy; or 4) Ultraviolet B + cannabinoid (e.g., dronabinol) | Cholestasis |
| 1) Counterirritant (e.g., capsaicin) + ultraviolet B phototherapy + optional activated charcoal + optional low pH moisturizer; or 2) Kappa opioid receptor agonist (e.g., nalfurafine) + optional ultraviolet B | Uremia (uremic pruritus) |
| Ultraviolet B phototherapy | Aquagenic dermatitis, atopic dermatitis, HIV/AIDS and prurigo nodularis |
| Ultraviolet A phototherapy + psoralen | Eczema, psoriasis, vitiligo and cutaneous T-cell lymphoma |
| 1) Ultraviolet A phototherapy + psoralen; or 2) SSRI (e.g., paroxetine), aspirin &/or interferon alpha | Polycythemia vera |
| Serotonin receptor antagonist (e.g., ondansetron) (concurrent with opioid) + opioid receptor antagonist (e.g., nalbuphine) (concurrent with opioid) | Spinal opioid-induced pruritus |
| Antipsychotic (e.g., pimozide) + SSRI (e.g., fluvoxamine) | Pruritic psychiatric disorders (e.g., neurotic excoriation) |

Use of Serlopitant as a Sleep Aid

The invention also encompasses the use of serlopitant as a sleep aid. Accordingly, the invention provides a method of aiding sleep, comprising administering to a subject suffering from a sleep problem or disorder an effective amount of serlopitant or a pharmaceutically acceptable salt, solvate or polymorph thereof. An additional sleep-aiding agent optionally can also be administered to the subject.

Serlopitant can aid sleep in subjects who suffer from a sleep disorder or a sleep problem in general. As a sleep aid, serlopitant may have a sedative effect (reducing irritability, anxiety or excitement) and/or a hypnotic effect (inducing, sustaining and/or lengthening sleep).

Examples of sleep disorders that serlopitant can potentially alleviate include without limitation insomnia (including primary and secondary insomnia, and transient, acute and chronic insomnia); sleeping sickness (African trypanosomiasis); circadian rhythm sleep disorders (e.g., advanced sleep phase disorder [ASPD], delayed sleep phase disorder [DSPD], irregular sleep wake rhythm, non-24 hour sleep-wake disorder, jet lag and shift work sleep disorder [SWSD]); parasomnias (e.g., bruxism, rapid eye movement sleep behavior disorder [RBD], periodic limb movement disorder [PLMD or nocturnal myoclonus], restless legs syndrome [RLS], sleep paralysis, exploding head syndrome, sleep terror [night terror or *Pavor nocturnus*], nocturia, nocturnal eating syndrome, sleep talking [somniloquy], sleepwalking [somnambulism] and somniphobia); and breathing-related sleep disorders (e.g., sleep apnea [including central, obstructive and mixed sleep apnea], hypopnea syndrome, sleep-related hypoventilation, snoring and upper airway resistance syndrome).

For use as a sleep aid, serlopitant is administered when the subject desires to sleep (e.g., at night or around bedtime). An effective amount of serlopitant is administered to aid sleep. The effective amount may depend on various factors, including the mode of administration; the age, body weight, general health, sex and diet of the subject; the severity of the sleep problem; and the response of the subject to the treatment. In certain embodiments, the dose of serlopitant as a sleep aid is about 0.1-500 mg, or about 0.25-400 mg, or about 0.5-300 mg, or about 1-200 mg, or about 2.5-100 mg, or about 5-50 mg, or as deemed appropriate by the treating physician. A single dose or multiple doses of serlopitant can be administered to aid sleep. In further embodiments, the dosage of serlopitant to aid sleep is about 0.01-10 mg/kg, 0.025-7.5 mg/kg, 0.05-5 mg/kg, 0.075-2.5 mg/kg or 0.1-1 mg/kg body weight, or as deemed appropriate by the treating physician.

Serlopitant can be administered via any suitable route. Potential routes of administration of serlopitant include without limitation oral, parenteral (including intramuscular, subcutaneous, intradermal, intravenous, intraarterial, intramedullary and intrathecal), intraperitoneal, and topical (including dermal/epicutaneous, transdermal, mucosal, transmucosal, intranasal [e.g., by nasal spray or drop], intraocular [e.g., by eye drop], pulmonary [e.g., by inhalation], buccal, sublingual, rectal and vaginal). In certain embodiments, serlopitant is administered orally.

In other embodiments, serlopitant is administered topically via a buccal or sublingual tablet or pill. The buccal or sublingual tablet or pill can be designed to provide faster release of serlopitant for more rapid uptake of it into systemic circulation. In addition to a therapeutically effective amount of serlopitant, the buccal or sublingual tablet or pill can contain suitable excipients, including without limitation any combination of fillers and diluents (e.g., mannitol and sorbitol), binding agents (e.g., sodium carbonate), wetting agents (e.g., sodium carbonate), disintegrants (e.g., crospovidone and croscarmellose sodium), lubricants (e.g., silicon dioxide [including colloidal silicon dioxide] and sodium stearyl fumarate), stabilizers (e.g., sodium bicarbonate), flavoring agents (e.g., spearmint flavor), sweetening agents (e.g., sucralose), and coloring agents (e.g., yellow iron oxide). A non-limiting example of a patient population that can benefit from a buccal or sublingual tablet or pill of a sleep aid is patients who wake up prematurely and have difficulty falling asleep again.

In some embodiments, an (one or more) additional sleep-aiding agent is administered in combination with serlopitant to aid sleep. The additional sleep-aiding agent can be administered concurrently with or sequentially to (before or after) administration of serlopitant. If administered concurrently with serlopitant, the additional sleep-aiding agent can be contained in the same composition as serlopitant or in separate compositions. Use of serlopitant may reduce the dosage of and/or the length of treatment with the additional sleep-aiding agent which would otherwise be required and thereby minimize or avoid any adverse effects (e.g., dependence or addiction) of the additional sleep-aiding agent.

The additional sleep-aiding agent can be selected for its soporific property or for its ability to treat the sleep disorder or the underlying cause of the sleep disorder (e.g., stress, anxiety, depression or a neurological condition). In some embodiments, the additional sleep-aiding agent is selected from the group consisting of hypnotics, sedatives, anxiolytics, antipsychotics and antidepressants. A particular sleep-aiding agent can have pharmacological effects that fall in multiple categories (e.g., benzodiazepines can have a sedative or anxiolytic effect at a lower dose and a hypnotic effect at a higher dose). In further embodiments, the additional sleep-aiding agent is selected from the group consisting of:
 antidepressants, including tricyclic antidepressants (e.g., amitriptyline, amitriptylinoxide, amoxapine, clomipramine, desipramine, dosulepin [dothiepin], doxepin, imipramine, lofepramine, melitracen, nortriptyline, protriptyline and trimipramine), tetracyclic antidepressants (e.g., amoxapine, maprotiline, mazindol, mianserin, mirtazapine and setiptiline), selective serotonin reuptake inhibitors (SSRIs, e.g., citalopram, dapoxetine, escitalopram, fluoxetine, fluvoxamine, paroxetine and sertraline), serotonin antagonist and reuptake inhibitors (SARIs, e.g., etoperidone, lorpiprazole, lubazodone, mepiprazole, nefazodone and trazodone), serotonin-norepinephrine reuptake inhibitors (SNRIs, e.g., bicifadine, duloxetine, milnacipran, levomilnacipran, sibutramine, venlafaxine, desvenlafaxine and SEP-227162), and monoamine oxidase (MAO) inhibitors (including selective MAO-A inhibitors, such as moclobemide, pirlindole [pirazidol] and toloxatone [humoryl]), and analogs and derivatives thereof;
 antipsychotics, including first-generation (or typical) antipsychotics (including phenothiazines [e.g., chlorpromazine, fluphenazine, levomepromazine, perazine, pericyazine, perphenazine, pipotiazine, prochlorperazine, promazine, promethazine, thioproperazine, thioridazine and trifluoperazine] and thioxanthenes [e.g., clopenthixol, zuclopenthixol, flupentixol and thiotixene]) and second-generation (or atypical) antipsychotics (e.g., amisulpride, aripiprazole, asenapine, clozapine, iloperidone, loxapine, amoxapine, lurasidone, olanzapine, quetiapine, norquetiapine, risperidone, paliperidone, sertindole, trimipramine, ziprasidone and zotepine), and analogs and derivatives thereof;
 antihistamines that inhibit action at the histamine $H_1$ receptor, including first-generation antihistamines such as alimemazine (trimeprazine), antazoline, azatadine, bromazine, carbinoxamine, chlorpromazine, clemastine, clocinizine, cyclizine, chlorcyclizine, cyproheptadine, dimenhydrinate, dimetindene, diphenhydramine, bromodiphenhydramine, chlorodiphenhydramine, doxylamine, hydroxyzine, meclizine, mepyramine [pyrilamine], methdilazine, oxatomide, phenindamine, pheniramine, brompheniramine, chlorpheniramine, fluorpheniramine, orphenadrine, phenyltoloxamine, promethazine, tripelennamine and triprolidine, and analogs and derivatives thereof;
 benzodiazepines that enhance the effect of gamma-aminobutyric acid (GABA) at the $GABA_A$ receptor by positive allosteric modulation of the receptor, such as adinazolam, alprazolam, chlordiazepoxide, climazolam, clonazepam, clorazepate, diazepam, estazolam, etizolam (a benzodiazepine analog), flunitrazepam, flurazepam, halazepam, loprazolam, lorazepam, lormetazepam, midazolam, nimetazepam, nitrazepam, oxazepam, prazepam, quazepam, temazepam and triazolam, and analogs and derivatives thereof;

non-benzodiazepines (also called Z-drugs) that are positive allosteric modulators of the $GABA_A$ receptor, such as beta-carbolines (e.g., abecarnil, gedocarnil and ZK-93423), cyclopyrrolones (e.g., pagoclone, pazinaclone, suproclone, suriclone, zopiclone and eszopiclone,), imidazopyridines (e.g., alpidem, necopidem, saripidem and zolpidem), pyrazolopyrimidines (e.g., divaplon, fasiplon, indiplon, lorediplon, ocinaplon, panadiplon, taniplon and zaleplon), and triazolopyridazines (e.g., CL-218,872), and analogs and derivatives thereof;

barbiturates that are positive allosteric modulators of the $GABA_A$ receptor, such as allobarbital, amobarbital, aprobarbital, alphenal, barbital, brallobarbital, butabarbital, mephobarbital, pentobarbital, phenobarbital, secobarbital and sodium thiopental, and analogs and derivatives thereof;

GABA analogs, such as gabapentin and pregabalin, and analogs and derivatives thereof;

melatonin receptor (e.g., $MT_1$ and/or $MT_2$) agonists, such as melatonin, agomelatine, LY-156,735, piromelatine, ramelteon and tasimelteon, and analogs and derivatives thereof;

orexin receptor (e.g., $OX_1$ and/or $OX_2$) antagonists, such as almorexant, suvorexant, SB-334,867, SB-408,124, SB-649,868, TCS-OX2-29, and N-Ethyl-2-[(6-methoxy-pyridin-3-yl)-(toluene-2-sulfonyl)-amino]-N-pyridin-3-ylmethyl-acetamide (EMPA), and analogs and derivatives thereof;

4-quinazolinones, such as afloqualone, cloroqualone, diproqualone, etaqualone, mebroqualone, mecloqualone, methaqualone, methylmethaqualone and nitromethaqualone, and analogs and derivatives thereof;

opioids (e.g., for pain-associated sleep disorders), such as buprenorphine, codeine, fentanyl, hydrocodone, hydromorphone, levorphanol, methadone, morphine, ethylmorphine, oxycodone, oxymorphone, pethidine, propoxyphene, dextropropoxyphene, thebaine and tramadol, and analogs and derivatives thereof;

herbs, such as *Cannabis* (including cannabinoids such as cannabidiol [CBD] and tetrahydrocannabinol [THC]), *Duboisia hopwoodii* (pituri), *Humulus lupulus* (hops), *Hypericum perforatum* (St. John's wort), *Lactuca virosa* (opium lettuce), *Lavandula* (lavender), *Matricaria chamomilla* (chamomile), *Nepeta cataria* (catnip), *Passiflora* (passion flowers) (e.g., *P. incarnata*), *Piper methysticum* (kava), *Prostanthera striatiflora* (striped mintbush), *Sceletium tortuosum* (kanna), *Scutellaria* (skullcaps) (e.g., *S. canescens, S. cordifolia, S. galericulata* and *S. lateriflora*), *Valeriana officinalis* (valerian), and *Withania somnifera* (ashwagandha); and other kinds of substances, such as S-adenosyl-L-homocysteine, L-tryptophan, L-arginine-L-aspartate, delta sleep-inducing peptide (DSIP), chloral hydrate, ethanol, 2-methyl-2-butanol, gamma-hydroxybutyric acid (GHB), glutethimide, medetomidine, dexmedetomidine, menthyl isovalerate (validol), S32212, $\alpha_2$ adrenergic agonists (e.g., clonidine), and carbonic anhydrase inhibitors (e.g., acetazolamide and topiramate), and analogs and derivatives thereof.

The additional sleep-aiding agent can also be selected for its ability to treat a condition that contributes to sleep difficulty (e.g., abnormal bodily movement or behavior). For example, an anticonvulsant can be used in combination with serlopitant to treat a parasomnia, such as restless legs syndrome, periodic limb movement disorder or nocturnal eating syndrome. Examples of anticonvulsants include without limitation carbamazepine, gabapentin, pregabalin, valproic acid and salts thereof (e.g., sodium valproate), and analogs and derivatives thereof.

The additional sleep-aiding agent can be administered via any suitable mode. In certain embodiments, the additional sleep-aiding agent is administered orally, bucally or sublingually.

Therapeutic Administration and Doses

The terms "administration of" or "administering a" compound should be understood to mean providing a compound of the invention to the individual in need of treatment in a form that can be introduced into that individuals body in a therapeutically useful form and therapeutically effective amount, including, but not limited to, oral dosage forms, such as tablets, capsules, syrups, suspensions, and the like.

The terms "treat", "treating" and "treatment" of chronic pruritus all refer to reducing the frequency of symptoms of acute or chronic pruritus (including eliminating them entirely), avoiding the occurrence of acute or chronic pruritus and/or reducing the severity of symptoms of acute or chronic pruritus.

The term "therapeutically effective amount" refers to a sufficient quantity of the compounds of the present invention, in a suitable composition, and in a suitable dosage form to treat the noted disease conditions. The "therapeutically effective amount" will vary depending on the compound, the severity of the condition causing the pruritus, and the age, weight, etc., of the patient to be treated.

The term "loading dose" refers to the amount of the compounds or compositions of the present invention that is often larger than subsequent doses, administered for the purpose of establishing a therapeutic level of the drug. More generally, a loading dose is the amount of Compound I, or a pharmaceutically acceptable salt, solvate or polymorph thereof, administered to a patient with pruritus given sometime after presentation but before initiation of one or more maintenance doses. Alternatively, a loading dose refers to one or a series of doses that may be given at the onset of therapy to achieve a target concentration of an active ingredient quickly.

The present methods for treatment of pruritus require administration of serlopitant, or a pharmaceutical composition containing serlopitant, to a patient in need of such treatment. The compound and/or pharmaceutical compositions are preferably administered orally. Various delivery systems are known, (e.g., encapsulation in liposomes, microparticles, microcapsules, capsules, etc.) can be used to administer a serlopitant compound and/or composition. The compound and/or pharmaceutical compositions may be delivered via sustained release dosage forms.

The amount of serlopitant, a pharmaceutically acceptable salt, solvate or polymorph thereof, that will be effective in the treatment pruritus in a patient will depend on the specific nature of the condition, and can be determined by standard clinical techniques known in the art. In addition, in vitro or in vivo assays may optionally be employed to help identify optimal dosage ranges. The specific dose level for any particular individual will depend upon a variety of factors including the activity of the composition, the age, body weight, general physical and mental health, genetic factors, environmental influences, sex, diet, time of administration, route of administration, rate of excretion, and the severity of the pruritus being treated.

Preferably, the dosage forms are adapted to be administered to a patient three, two or one time a day. More preferably, a therapeutically effective amount is taken once per day. Alternatively, a dose may be taken every other day, every third day, every fourth day or once a week. In some embodiments, serlopitant is administered under a chronic dosing regimen. In certain embodiments, a therapeutically effective amount of serlopitant is administered over a period of at least 2 weeks, 3 weeks, 1 month, 1.5 months, 2 months, 3 months, 4 months, 5 months, 6 months or longer.

Doses may be taken at any time convenient to the patient. However, to minimize side effects such as dizziness or drowsiness, a daily dose may be taken at bedtime. NK-1 receptor antagonists have been shown to cause drowsiness in human clinical trials for uses other than treating pruritus. For example, Ratti et al. reported as much as a doubling in the incidence of somnolence vs. placebo in patients treated with casopitant for major depressive disorder (*J. Clin. Psychopharmacol.*, 2011, 31:727-733). Somnolence was also seen in a similar clinical trial testing NK-1 receptor antagonist L-759274 as an anti-depressant (M. S. Kramer et al., *Neuropsychopharm.*, 2004, 29:385-392). Thus, in one embodiment of the present invention, serlopitant is administered before the patient goes to bed.

Dosing may be provided alone or in combination with other drugs and may continue as long as required for effective treatment pruritus. For example, the compounds of the present invention may be administered in combination with another substance that has a complimentary effect to the tachykinin and substance P inhibitory effect of the present invention. Appropriate compounds include other NK-1 receptor antagonists such as, but not limited to, casopitant (GW679769), L-759274, L-733060, CP122,721, BIIF 1149CL, DNK333, M516102, ezlopitant, rolapitant, orvepitant, LY-686017, lanepitant (LY-303870), maropitant, vestipitant, vofopitant, aprepitant, fosaprepitant, AV-818, and TA-5538.

Dosage ranges of compounds of the present invention for oral administration may be stated in terms of amount of drug administered per time period. A certain amount of active ingredient may be given one or more times a day as appropriate according to the factors described above. For example, doses may be taken once a day, twice a day, three times a day, four times a day, or more. Suitable dosages range from about 0.1 mg to about 30 mg, and preferably, from about 1 mg to about 7.5 mg. Suitable dosages are typically 0.10 mg, 0.15 mg, 0.20 mg, 0.25 mg, 0.5 mg, 0.75 mg, 1 mg, 2 mg, 2.5 mg, 3 mg, 4 mg, 5 mg, 6 mg, 7 mg, 8 mg, 9 mg, 10 mg, 15 mg, 20 mg, 25 mg, 30 mg, 35 mg, 40 mg, 50 mg, 100 mg or 200 mg one or more times a day. Preferably, a dose of 0.25 mg, 1 mg or 5 mg is administered once a day.

Alternatively, suitable dosage ranges of compounds of the present invention for oral administration are generally about 0.001 mg to about 500 mg of drug per kilogram body weight, preferably from about 0.1 mg to about 200 mg of drug per kilogram body weight, and more preferably about 1 to about 100 mg/kg-body wt. per day. Dosage ranges may be readily determined by methods known to the skilled artisan. The amount of active ingredient that may be, for instance, combined with carrier materials to produce a single dosage form will vary depending upon the patient treated and the particular mode of administration. Dosage unit forms will generally contain between about 0.25 mg to about 500 mg of active ingredient.

In cases in which longer-term persistence of active drug is desirable, for example but not limited to, in the treatment of chronic pruritus, a dosing schedule is used where a loading dose is administered, followed by either (i) a second loading dose, or doses, and a maintenance dose (or doses), or (ii) a maintenance dose or doses, without a second loading dose, as determined to be appropriate by one skilled in the art. The schedule for administration of the loading and maintenance doses may be determined based upon the individual requirements of a particular patient. In one embodiment of the present invention, one loading dose is administered, followed by administration of a therapeutically effective maintenance dose after an appropriate interval, such as after one day. In another embodiment, a loading dose is administered on day 1, a second loading dose on day 2, and the maintenance dose is administered on day 3 and thereafter for the duration of therapy. The loading dose may be five, four, three or two times the maintenance dose. Preferably, the loading dose is three times the maintenance dose. The active drug can be administered via any suitable mode (e.g., orally).

Determination of Therapeutic Effectiveness

The effectiveness of compositions of the present invention can be tested in experimental animal models of pruritus known to those skilled in the art. For example, various mouse models have been utilized to evaluate treatments for itching. Tsukumo et al. describe a model in which 4-ethoxymethylene-2-phenyl-2-oxazolin-5-one (oxazolone) induces chronic dermatitis with an associated itch response in BALB/c mice that can be used to determine whether an anti-pruritic treatment is effective (*J. Pharmacol. Sci.*, 2010, 113:255-262). Costa et al. report a similar model in which *Phoneutria nigriventer* spider venom is used as the itch inducer (*Vascul. Pharmacol.*, 2006, 45(4):209-14). Analogously, Ohmura et al. use picrylchloride in NC/Nga mice to stimulate scratching behavior (*Eur. J. Pharmacol.*, 2004; 491:191-194). Essentially, itching is induced in the subject animal with an irritating agent, the test compound or a placebo is administered, and the animal observed under controlled conditions. Scratching behavior is quantified and analyzed using standard statistical techniques. A test compound is considered effective if either continuous or severe scratching is suppressed.

The efficacy of the methods and compositions of the present invention in the treatment of acute and chronic pruritus can also optionally be evaluated in human clinical trials conducted under appropriate standards and ethical guidelines as set forth by the U.S. Food and Drug Administration (FDA). After the general safety of a drug is determined in Phase I clinical trials conducted in healthy volunteers, Phase II trials assessing the safety and efficacy of the drug in patients with the condition being treated are conducted. Typically, such trials are double-blinded and placebo-controlled, and may be dose-ranging. Phase III studies gather more information about safety and effectiveness by studying different populations and different dosages and by using the drug in combination with other drugs.

Because amelioration of pruritus is subject to a patient's own perceptions, it can be difficult to evaluate with typical clinical endpoints. However, two standardized assessment tools have been created and may be used in clinical trials demonstrating the utility of the present invention. The Visual Analog Scale (VAS) is the most commonly used tool to evaluate the intensity of pruritus (N. Q. Phan et al., *Acta Derm. Venereol.*, 2012; 92:502-507). The VAS is a graphic tool with a 100-mm horizontal line with the left end labeled "no symptom" and the right end labeled "worst imaginable symptom". The patient is asked to draw a vertical line to indicate the horizontal scale at a point that corresponded to the intensity of the symptom. The length from the left end to the vertical mark made by the patient is measured in millimeters. Separation in one-hundredths is regarded as sufficiently sensitive (R. C. Aitken, *Proc. R. Soc. Med.*, 1969, 62:989-993). The results may be analyzed using standard statistical techniques known to those skilled in the art.

In addition to the VAS, the Dermatology Life Quality Index (DLQI) may be used to evaluate the efficacy of a chronic pruritus treatment. The DLQI, a self-administered general dermatology quality of life questionnaire, was originally developed and published in a dermatology clinic at University Hospital of Wales (A. Y. Finlay and G. K. Khan, Clin. Exper. Derm., 1994, 19:210-216). Independent studies have verified that the DLQI is an easy and efficient method for assessing quality of life in dermatology patients (H. B. Hahn et al., J. Am. Acad. Dermatol., 2001, 45(1):44-8). A current version of the simple, ten-question validated questionnaire, with instructions for use and scoring is available from the School of Medicine, Cardiff University, Wales, UK (world wide web URL dermatology.org.uk/quality/).

The following examples are offered by way of illustration and not by way of limitation.

EXAMPLES

All of the inactive pharmaceutical ingredients in the examples below comply with United States Pharmacopeia and The National Formulary requirements and are tested and released according to the monograph for each ingredient specified in the USP/NF compendium.

Example 1. Preparation of Serlopitant Tablets

Serlopitant, 3-[(3aR,4R,5S,7aS)-5-[(1R)-1-[3,5-bis(trifluoromethyl)phenyl]ethoxy]-4-(4-fluorophenyl)-1,3,3a,4,5,6,7,7a- octahydroisoindol-2-yl]cyclopent-2-en-1-one, Compound 1, may be formulated as a tablet for oral use. Table 1 shows the qualitative/quantitative composition of exemplary dosages. Minor variations in the excipient quantities (+/−10%) may occur during the drug development process.

TABLE 1

| Components | Function | % of composition |
| --- | --- | --- |
| Compound 1 | Active agent | 1-6% |
| Microcrystalline cellulose | Diluent | 50-60% |
| Mannitol | Diluent | 20-30% |
| Croscarmellose Sodium | Disintegrant | 1-3% |
| Colloidal silica | Disintegrant | 0.25-0.5% |

TABLE 1-continued

| Components | Function | % of composition |
| --- | --- | --- |
| Sodium Lauryl Sulfate | Surfactant | 5-6% |
| Magnesium Stearate | Lubricant | 0.25-2% |
| Total Tablet Composition | | 100% |

Tablet potencies of 0.25, 1 and 5 mg are prepared as a compressed tablet formulation. The tablet manufacturing process is the same for all proposed potencies. The process consists of the following steps: 1) Compound 1, mannitol and sodium lauryl sulfate are blended; 2) the remaining mannitol is added to the blender and mixed; 3) microcrystalline cellulose, croscarmellose sodium, and colloidal silica are added to the blender containing the mixture above to complete the mixing and the blend is de-agglomerated if necessary; 4) the blend is lubricated with magnesium stearate which has been previously screened, if necessary; 5) the lubricated blend is roller compacted and milled, and then lubricated with magnesium stearate, which has been previously screened, if necessary; and 6) the mixture is then compressed into tablets of the appropriate weight.

Example 2. Preparation of Serlopitant Capsules

Serlopitant (Compound 1) may also be supplied to the clinic as liquid-filled capsules. Table 2 shows the qualitative/quantitative composition of exemplary dosages. Minor variations in the excipient quantities (+/−10%) may occur during the drug development process.

TABLE 2

| | | Unit Strength | | |
| --- | --- | --- | --- | --- |
| Components | Function | 0.25 mg | 1 mg | 4 mg |
| Capsule Fill | | | | |
| Compound 1 | Active agent | 0.25 mg | 1 mg | 4 mg |
| Mono- & Di-glycerides | Solubilizer | 399 mg | 398.6 mg | 395.6 mg |
| Butylated Hydroxyanisole | Antioxidant | 0.40 mg | 0.40 mg | 0.40 mg |
| Capsule Shell | | | | |
| #0 White Opaque Hard Gelatin Capsule* | Capsule shell | 96 mg** | 96 mg** | 96 mg** |
| Gelatin*** | Banding component | — | — | — |
| Polysorbate 80*** | Banding component | — | — | — |

*Capsules are provided by Capsugel (Morristown, NJ) and contain gelatin and titanium dioxide
**Approximate weight of empty capsule shell
***As needed to seal the capsule shells The formulation is prepared by dissolving the drug substance in mono- and di-glycerides. Furthermore, 0.1 wt % butylated hydroxyanisole is added as an antioxidant. Initial capsule strengths are dispensed into hard gelatin capsules and sealed by spraying with a 1:1 (wt/wt) water:ethanol solution. Subsequent potencies including 0.25, 1, and 4 mg are dispensed into hard gelatin capsules and sealed with a band of gelatin/polysorbate 80. Corresponding placebo formulations are prepared in a similar manner, but without the addition of the drug substance and the antioxidant.

The capsule manufacturing process is the same for all potencies. The process consists of the following steps: 1) the mono- and di-glycerides excipient is melted at 40° C., if necessary; 2) the mono- and diglycerides are added to an appropriately sized, jacketed vessel and mixing is initiated;

3) the butylated hydroxyanisole is added to the mono- and di-glycerides and mixed until dissolved (minimum of 10 min); 4) Compound 1 is slowly added to the mixture and mixed until dissolved (visual confirmation); 5) the solution is filled into hard gelatin capsules; 6) the filled capsules are sealed with a mixture of gelatin and polysorbate 80; 7) the sealed capsules are allowed to dry overnight and then the capsules are visually inspected for leaking; 8) the acceptable capsules may be weighed sorted, if necessary; and 9) the finished product is then packaged in appropriate containers.

Example 3. Clinical Study of Serlopitant in Chronic Pruritus

A well-controlled human clinical trial testing the efficacy of three dosages of serlopitant in the treatment of chronic pruritus is conducted in accordance with the ICH Guidelines for Good Clinical Practices, the U.S. Code of Federal Regulations, the Health Insurance Portability and Accountability Act (HIPAA), and any local regulatory requirements. The study is a Phase II randomized, double-blind, parallel group, placebo-controlled, multicenter trial designed to test the efficacy and safety of several doses of serlopitant versus placebo in patients with chronic pruritus. The study patient population includes adult, males or females, 18 to 72 years of age. The patients must be previously diagnosed with chronic pruritus caused by any etiology, except uremia, hepatic failure, cancer or cancer therapy, with chronic pruritus defined as greater than 6 weeks of itching and a VAS score of greater than 7.

Patients are randomized to receive either placebo or one of three doses of active agent. Patients take active drug or placebo once daily by mouth for a total of 2 to 8 weeks. The maximum study duration for each subject is approximately 14 weeks and includes a screening period of up to 2 weeks, a treatment period of 2-8 weeks, and a follow-up period of up to 4 weeks. The study parameters are summarized in Table 3.

Additional clinical trials according to a similar design may be conducted to test different dosage levels of the active ingredient or to differentiate between optimal doses or dosing schedules. Further, the efficacy of the drug in specific populations, such as the elderly, children, or patients with uremia, hepatic failure, cancer or patients undergoing cancer therapy, may be determined in additional clinical trials conducted in a similar fashion.

Example 4. Topical Formulations Containing Serlopitant

Table 5 shows various topical formulations containing serlopitant. The formulations contain Vanicream™ Moisturizing Skin Cream ("VM"), Vanicream™ Lite Lotion ("VLL") or Aquaphor® Healing Ointment ("AP", from Eucerin) as the base or carrier. VM and VLL are oil-in-water emulsion and AP has an oil base. A stock solution of free base serlopitant (Compound 1, or "Cpd 1") in ethanol (EtOH) was prepared by dissolving free base serlopitant in ethanol to the maximum extent and then filtering the resulting solution through an Anotop® 25 inorganic filter having a 0.02 micron pore size. Free base serlopitant has a maximum solubility in ethanol of 64.5 mg/g EtOH, or 6.45% w/w. To prepare a topical formulation, the stock solution of serlopitant/ethanol was added to a tared tube containing a particular amount of the base until the resulting mixture weighed 25.0 g. The mixture was mixed vigorously for 2 minutes using a vibration stand and then was rotated slowly for 4 days. For the "C" formulations, ethanol containing no serlopitant was added so that the "B" and "C" formulations would contain the same amount of base and ethanol.

TABLE 5

| Mixture | Lot Size (g) | Base (g) | Cpd 1/EtOH Stock Soln (g) | Blank EtOH (g) | % Cpd 1 (w/w) | % EtOH (w/w) |
|---|---|---|---|---|---|---|
| VM-A | 25.0 | 23.06 | 1.94 | 0.0 | 0.5 | 7.8 |
| VM-B | 25.0 | 21.12 | 3.88 | 0.0 | 1.0 | 15.5 |

TABLE 3

| | |
|---|---|
| Study Title: | Phase II Study of Serlopitant In Patients with Chronic Pruritus |
| Development Phase: | Phase II |
| Study Objectives: | Dose finding, efficacy and safety |
| Study Design: | Multicenter, double blind, parallel group, dose finding |
| Sample Size: | 80-240 subjects evaluable for analysis |
| Study Population: | Patients with chronic pruritus (over 6 weeks duration) unresponsive to standard treatment |
| Investigational Product: | Oral daily tablet Dosage and frequency: Day 1: loading dose of 3 times of drug dose (0.25 mg, 1 mg, or 5 mg), followed by Drug A, Drug B, or Drug C Drug A: 0.25 mg serlopitant daily for 2 to 8 weeks Drug B: 1 mg serlopitant daily for 2 to 8 weeks Drug C: 5 mg serlopitant daily for 2 to 8 weeks |
| Reference Product(s): | None |
| Control Product(s): | Matching placebo daily for 2 to 8 weeks |
| Efficacy Evaluation Criteria: | Efficacy is measured daily by patient diary. Patients record pruritus level on a 10 point VAS scale. Clinical response is measured by a change in VAS score between the active agent and the placebo. Secondary endpoints will include measures of the Dermatology Life Quality Index (DLQI), lesion healing, and patient and physician global assessments. |
| Safety Evaluation Criteria: | All local and systemic adverse events observed by or reported to the investigators are evaluated. The intensity, duration, and causal relationship to the study product are rated for all adverse events. |
| Statistical Methods: | The primary study endpoint is the difference in VAS score at baseline and on treatment between placebo and active agent. |
| Study Sites: | Multicenter |

TABLE 5-continued

| Mixture | Lot Size (g) | Base (g) | Cpd 1/EtOH Stock Soln (g) | Blank EtOH (g) | % Cpd 1 (w/w) | % EtOH (w/w) |
|---|---|---|---|---|---|---|
| VM-C | 25.0 | 21.12 | 1.94 | 1.94 | 0.5 | 15.5 |
| VLL-A | 25.0 | 23.06 | 1.94 | 0.0 | 0.5 | 7.8 |
| VLL-B | 25.0 | 21.12 | 3.88 | 0.0 | 1.0 | 15.5 |
| VLL-C | 25.0 | 21.12 | 1.94 | 1.94 | 0.5 | 15.5 |
| AP-A | 25.0 | 23.06 | 1.94 | 0.0 | 0.5 | 7.8 |
| AP-B | 25.0 | 21.12 | 3.88 | 0.0 | 1.0 | 15.5 |
| AP-C | 25.0 | 21.12 | 1.94 | 1.94 | 0.5 | 15.5 |

AP was determined to be an unsuitable base for an ethanol solution containing serlopitant because of ethanol insolubility in that base. The VM base appeared stable/unchanged under 15× microscopic magnification after 4 days of mixing with 15.5% ethanol. The VLL base showed some aggregation of lamellar structures under 15× microscopic magnification after 4 days of mixing with 15.5% ethanol, but the overall change to the base appeared minor. The VM and VLL formulations can be tested, e.g., for the skin permeation of serlopitant.

Example 5. In Vitro Skin Permeation of Serlopitant in Topical Formulations

Topical formulations A-D used in the in vitro skin permeation studies are shown in Table 6. The bases "VM" and "VLL" of formulations A-D are described in Example 4. Formulations A-D were prepared according to the procedures described in Example 4.

TABLE 6

| Formul'n (Base) | Final Mass (g) | Base (g) | Cpd 1/EtOH Stock Soln (g) | Blank EtOH (g) | % Cpd 1 (w/w) | % EtOH (w/w) |
|---|---|---|---|---|---|---|
| A (VM) | 25.28 | 21.27 | 0.0 | 4.01 | 0.0 | 15.9 |
| B (VLL) | 25.12 | 21.19 | 3.93 | 0.0 | 1.0 | 15.6 |
| C (VM) | 13.80 | 11.63 | 2.17 | 0.0 | 1.0 | 15.7 |
| D (VLL) | 25.02 | 21.15 | 0.0 | 3.87 | 0.0 | 15.5 |

Figure 2:
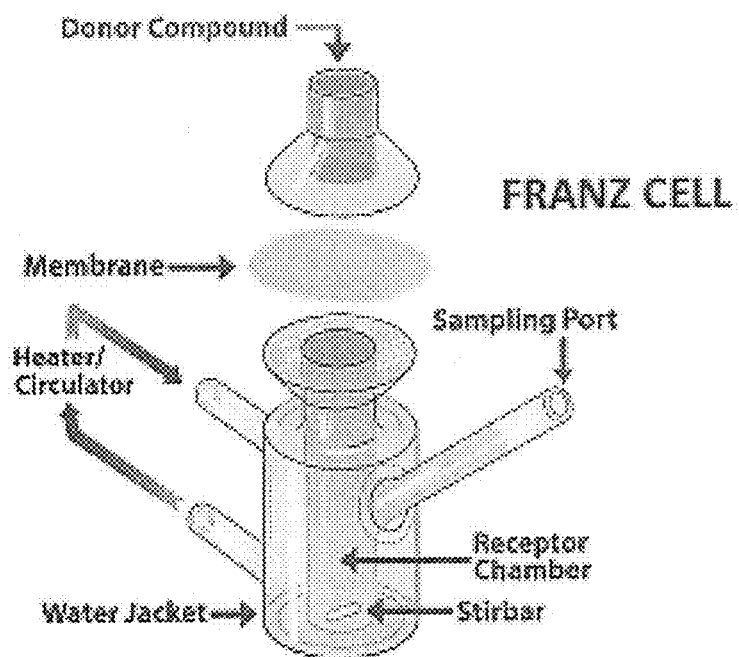
FIG. 2 illustrates a Franz diffusion cell for studying skin permeation of a drug in vitro.

In vitro skin permeation of serlopitant in topical formulations A-D was evaluated using a Franz diffusion cell. FIG. 2 illustrates a Franz diffusion cell. A Franz diffusion cell having a circular permeation area of 4.15 cm² and a receptor chamber volume of 19 mL was set up with a thermo-regulated outer water jacket to maintain the temperature at 37° C. The receptor chamber was filled with 19 mL 1×PBS (pH 7.5) containing 10% ethanol and 1% Tween® 80. Solubility test indicated that serlopitant remained soluble at concentrations of 0.5, 5 and 50 ug/mL in this solution after 1 hour of incubation at 37° C. The solubility of serlopitant decreased significantly if Tween® 80 was not used and decreased slightly if ethanol was not used.

Human skin was pretreated to remove all subcutaneous fat and was cleaned with 70% ethanol before use. The skin was visually inspected to ensure that it was free of any surface irregularity or small holes and was equally divided into four pieces. The skin was then mounted onto the receptor chamber with the stratum corneum side facing up. About 100 mg of topical formulation A, B, C or D was applied to the skin (actual weight: A, 103.8 mg; B, 101.3 mg; C, 103.2 mg; and D, 103.8 mg), which was then covered with parafilm to avoid evaporation.

About 0.5 mL of solution was withdrawn through the sampling port of the Franz diffusion cell at 0.5, 1, 2, 4, 6, 18 and 22 hours. The receptor chamber was replenished with equal volume of fresh diffusion buffer after each sampling. At the end of the experiment (after 22 hours of incubation), the skin was wiped clean with methanol, and the formulation-treated area was weighed and frozen for cryosectioning.

Figure 3:
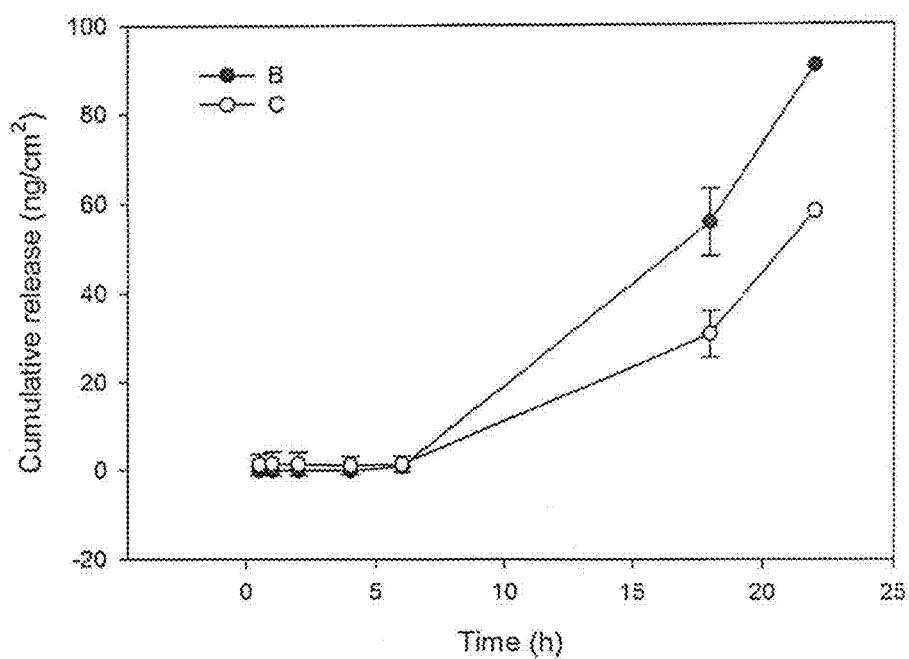
FIG. 3 shows the cumulative release of serlopitant from topical formulations B and C into the receptor chamber of a Franz diffusion cell at various time points in an in vitro study of skin permeation.

All samples were processed by solid-phase extraction (SPE) before LC-MS/MS analysis. Briefly, a Strata-X 33 um Polymeric Reverse-Phase column with 30 mg sorbent mass/1 mL volume (Phenomenex) was conditioned with 1 mL of methanol and equilibrated with 1 mL of water. 300 uL of sample was loaded to the column followed by a wash with 1 mL of 30% methanol. Serlopitant was eluted with 2% formic acid in acetonitrile. The sample then was concentrated by blow drying with nitrogen and re-suspended in 50 uL of 50% methanol. A working standard was first generated by spiking the diffusion buffer with known concentrations of serlopitant, which was then processed using the same SPE method. A sensitivity of 0.1 ng/mL was achieved. Serlopitant concentrations in samples resulting from formulations A-D were determined by comparison to the standard. Serlopitant was not detected in samples resulting from topical formulations A and D, as expected. FIG. 3 shows the cumulative release of serlopitant from topical formulations B and C into the receptor chamber at 0.5, 1, 2, 4, 6, 18 and 22 hours. After an initial lag, serlopitant was detected by LC-MS/MS in the receptor chamber at 6 hours. FIG. 3 indicates that topical formulation B resulted in greater penetration of serlopitant through the skin than topical formulation C in this in vitro study.

Figure 4:
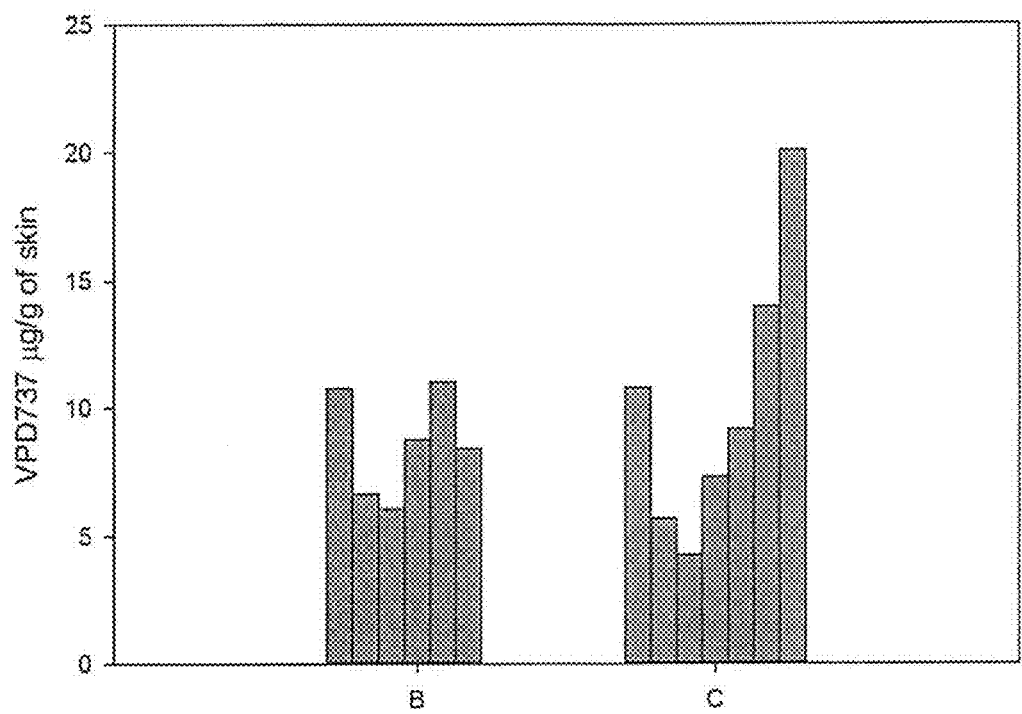
FIG. 4 shows the amount of serlopitant (called "VPD737") retained in the skin at the end of the Franz diffusion cell study. Each bar represents ug of serlopitant/g of skin in 250 um skin layers. For each of topical formulations B and C, the bars from left to right represent the amount of serlopitant retained in skin layers from the stratum corneum to the dermis.

The amount of serlopitant retained in the skin was determined at the end of the experiment. The skin was wiped and washed with methanol. The formulation-treated area was cut into horizontal sections of 25 um using a cryostat. Every 10 sections were pooled, placed in Eppendorf tubes, weighed and digested with twice the volume of 1 mg/mL liberase at 37° C. for 1 hour. Digested skin sections were further homogenized with a probe sonicator. To 25 uL of the skin homogenate were added 25 uL of 50% methanol and 100 uL of acetonitrile/methanol to extract serlopitant. For spiked standards, 25 uL of a solution of serlopitant in 50% methanol (from 5 ng/mL to 5000 ng/mL) was added to 25 uL of blank skin homogenate followed by 100 uL of acetonitrile/methanol. Extracted serlopitant was quantified by LC-MS/MS. FIG. 4 shows the amount of serlopitant (called "VPD737" in FIG. 4) retained in the skin at the end of the experiment. Each bar represents ug of serlopitant/g of skin in 250 um skin layers. For each of topical formulations B and C, the bars from left to right represent the amount of serlopitant retained in skin layers from the stratum corneum to the dermis.

Example 6. Representative Topical Formulations Containing Serlopitant

Table 7 provides non-limiting examples of topical formulations that can be prepared with serlopitant or a salt, solvate or polymorph thereof, and optionally an additional therapeutic agent.

TABLE 7

| Dosage Form | Ingredients in Addition to Serlopitant |
|---|---|
| cream | sorbitol, cetyl alcohol, isopropyl myristate, glyceryl stearate, PEG-100 stearate, petrolatum, benzyl alcohol, titanium dioxide and water |
| cream | propylene glycol, cetostearyl alcohol, Cremophor ® A6, Cremophor ® A25, liquid paraffin, parabens and water |
| cream | glycerol, sorbitol, isopropyl palmitate, emulsifying wax, benzyl alcohol, a pH adjuster (e.g., NaOH or lactic acid), and water |
| cream | glycerol, stearic acid, glyceryl monostearate, triethanolamine, parabens and water |
| cream | propylene glycol, cetostearyl alcohol, mineral oil, white petrolatum, ceteareth-30, chlorocresol, sodium phosphate monobasic, phosphoric acid, water, and optionally NaOH |
| cream | glycerol, cetostearyl alcohol, mineral oil, petrolatum, ceteth-20, diazolidinyl urea, dichlorobenzyl alcohol, edetic acid (EDTA) or disodium edetate, dibasic sodium phosphate and water |
| cream | propylene glycol, stearyl alcohol, white petrolatum, polysorbate 60, parabens, and optionally water |
| cream | propylene glycol, stearyl alcohol, cetyl alcohol, oleyl alcohol, mono-, di- and/or tri-glycerides, sodium cetostearyl sulphate, benzyl alcohol, citric acid, a pH adjuster (e.g., NaOH or lactic acid), and water |
| cream | hexylene glycol, stearyl alcohol, propylene glycol stearate, white wax, white petrolatum, aluminum starch octenylsuccinate, ceteareth-20, titanium dioxide, phosphoric acid and water |
| cream | propylene glycol, sorbitol, glyceryl monoisostearate, polyglyceryl-3 oleate, mineral oil, microcrystalline wax, colloidal silicon dioxide, parabens, EDTA or disodium edetate, and water |
| cream | propylene glycol, stearic acid, isopropyl palmitate, emulsifying wax, beeswax, polysorbate 60, an antioxidant (e.g., propyl gallate), a preservative (e.g., sorbic acid and/or potassium sorbate), a pH adjuster (e.g., NaOH and/or citric acid), and water |
| cream | cetostearyl alcohol, lanolin alcohols, isopropyl myristate, aluminum stearate, magnesium stearate, mineral oil, white petrolatum, water, and optionally disodium edetate and/or lactic acid |
| cream | propylene glycol, cetostearyl alcohol, white soft paraffin, liquid paraffin, lanolin, simethicone M30, Tween ® 60, parabens and water |
| cream | cetostearyl alcohol, mineral oil, white petrolatum, ceteth-20, parabens, citric acid, sodium citrate, and water |
| cream | propylene glycol, cetostearyl alcohol, polyoxyl 20 cetostearyl ether, mineral oil (liquid paraffin), petrolatum (white soft paraffin), chlorocresol, parabens, sodium phosphate monobasic, and water |
| cream | propylene glycol, cetostearyl alcohol, stearic acid, cetyl palmitate, sorbitan monostearate, mineral oil, polysorbate 60, benzyl alcohol and water |
| ointment | hexylene glycol, propylene glycol stearate, white wax, white petrolatum, phosphoric acid and water |
| ointment | propylene glycol, mineral oil, petrolatum, steareth-2, tocopherol, EDTA or disodium edetate, dibasic sodium phosphate and water |
| ointment | propylene glycol, fatty alcohol citrate, fatty acid pentaerythritol ester, sorbitan sesquioleate, white petrolatum, beeswax, aluminum stearate, butylated hydroxyanisole (BHA), citric acid, and optionally water |
| ointment | an alcohol (e.g., ethanol and/or propylene glycol), polyethylene or white petrolatum, mineral oil, and optionally water |
| gel | ethanol, carbomer 934P, triethanolamine and water |
| gel | glycerol, carbomer 940, poloxamer, dimethicone, disodium lauryl sulfosuccinate, silicon dioxide, a preservative (e.g., benzoyl peroxide and/or methyl paraben), EDTA or disodium edetate, a pH adjuster (e.g., NaOH or lactic acid), and water |
| gel | glycerol, hydroxy-beta-cyclodextrin, hydroxyethyl cellulose, parabens, EDTA or disodium edetate, and water |
| gel | propylene glycol, polyacrylic acid, medium-chain triglycerides, lecithin, polysorbate 80, a preservative (e.g., benzoic acid), EDTA or disodium edetate, a pH adjuster (e.g., NaOH or lactic acid), and water |
| gel | ethanol, isopropyl myristate, carbomer 940, triethanolamine, docusate sodium, EDTA or disodium edetate, and water |
| gel | propylene glycol, Carbopol ® 941, PEG 400, methyl paraben, a pH adjuster (e.g., NaOH or lactic acid), and water |
| gel | propylene glycol, PEG 400, carbomer 934P, allantoin, methyl paraben, a pH adjuster (e.g., NaOH or lactic acid), and water |
| gel | an alcohol (e.g., ethanol and/or propylene glycol), carbomer, dioctyl sodium sulfosuccinate, a preservative (e.g., benzoyl peroxide), a pH adjuster (e.g., NaOH or lactic acid), and water |
| gel | glycerol, propylene glycol, aloe vera gel, diazolidinyl urea, capryl/capramidopropyl betaine, parabens, citric acid, sodium citrate, and water |
| gel | ethanol, hydroxypropyl cellulose and water |
| lotion | glycerol, stearyl alcohol, glyceryl stearate, PEG-100 stearate, PEG 400, carbomer 941, cyclomethicone, light mineral oil, steareth-21, benzyl alcohol, sorbic acid or potassium sorbate, a pH adjuster (e.g., NaOH or lactic acid), and water |
| lotion | isopropanol, propylene glycol, hydroxypropyl cellulose, sodium phosphate monobasic, phosphoric acid and water |

TABLE 7-continued

| Dosage Form | Ingredients in Addition to Serlopitant |
|---|---|
| lotion | propylene glycol, cetyl alcohol, stearyl alcohol, glyceryl stearate, sorbitan monostearate, light mineral oil, sodium lauryl sulfate, parabens, EDTA or disodium edetate, water, and optionally a pH adjuster (e.g., NaOH or citric acid) |
| lotion | glycerol, cetostearyl alcohol, isostearyl alcohol, stearic acid, glyceryl stearate, sodium lauroyl sarcosinate, methyl paraben and water |
| suppository | an alcohol (e.g., ethanol and/or propylene glycol) and glycerides of saturated fatty acids |
| suppository | 95% ethanol and Suppocire ® AM (glyceride base containing saturated $C_8$-$C_{18}$ triglyceride fatty acids) |
| pledget | isopropanol, propylene glycol and water |
| foam | ethanol, propylene glycol, cetyl alcohol, stearyl alcohol, polysorbate 60, KOH and water, and pressurized with a propane/butane propellant |
| spray (dermal) | ethanol, undecylenic acid, isopropyl myristate, sodium lauryl sulfate, and water |
| spray (dermal) | glycerol, lactose, cetostearyl alcohol, mineral oil, ceteth-20 phosphate, dicetyl phosphate, urea, potassium phosphate monobasic, parabens, a pH adjuster (e.g., NaOH or lactic acid), and water |
| spray (nasal) | microcrystalline cellulose, carboxymethyl cellulose sodium, dextrose, polysorbate 80, disodium edetate, potassium sorbate, a pH adjuster (e.g., HCl), water, and optionally an alcohol (e.g., ethanol) |
| spray (nasal) | microcrystalline cellulose, carboxymethyl cellulose sodium, dextrose, polysorbate 80, benzalkonium chloride, phenylethyl alcohol, water, and optionally an alcohol (e.g., ethanol) |
| spray (nasal) | hypromellose, benzalkonium chloride, NaCl, EDTA, citric acid, sodium phosphate dibasic, water, and optionally an alcohol (e.g., ethanol) |

All publications and patent applications mentioned in this specification are herein incorporated by reference to the same extent as if each individual publication or patent application were specifically and individually indicated to be incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating pruritus associated with a burn, comprising administering a therapeutically effective amount of 3-[(3aR,4R,5S,7aS)-5-[(1R)-1-[3,5-bis(trifluoromethyl)phenyl]ethoxy]-4-(4-fluorophenyl)-1,3,3a,4,5,6,7,7a-octahydroisoindol-2-yl]cyclopent-2-en-1-one (serlopitant) or a pharmaceutically acceptable salt, solvate or polymorph thereof to a patient in need of treatment.

2. The method of claim 1, wherein the therapeutically effective amount of serlopitant comprises a dosage of 0.10 mg, 0.15 mg, 0.20 mg, 0.25 mg, 0.5 mg, 0.75 mg, 1 mg, 2 mg, 2.5 mg, 3 mg, 4 mg, 5 mg, 6 mg, 7 mg, 8 mg, 9 mg, 10 mg, 15 mg, 20 mg, 25 mg or 30 mg one or more times a day.

3. The method of claim 2, wherein the therapeutically effective amount of serlopitant comprises a dosage of 1 mg, 3 mg or 5 mg once a day.

4. The method of claim 1, wherein the therapeutically effective amount of serlopitant comprises a dosage of from about 0.1 mg to about 30 mg, or from about 1 mg to about 7.5 mg.

5. The method of claim 1, wherein serlopitant is administered once a day, once every other day, once every third day, once every fourth day, or once a week.

6. The method of claim 1, wherein serlopitant is administered over a period of at least 1 month, 1.5 months or 2 months.

7. The method of claim 1, wherein at least one loading dose of serlopitant is first administered, and at least one therapeutically effective maintenance dose of serlopitant is subsequently administered.

8. The method of claim 7, wherein the at least one loading dose is five times, four times, three times or two times larger than the at least one therapeutically effective maintenance dose.

9. The method of claim 1, wherein serlopitant is administered at bedtime.

10. The method of claim 1, wherein serlopitant is administered orally.

11. The method of claim 1, wherein serlopitant is administered topically.

12. The method of claim 11, wherein serlopitant is administered dermally or transdermally.

13. The method of claim 1, wherein the pruritus is chronic pruritus.

14. The method of claim 1, further comprising administering one or more additional antipruritic agents.

15. The method of claim 14, wherein the one or more additional antipruritic agents are selected from the group consisting of antihistamines, corticosteroids, immunomodulators, immunosuppressants, opioid receptor antagonists, antidepressants and anticonvulsants.

16. A method of treating pruritus associated with cutaneous T-cell lymphoma (CTCL), comprising administering a therapeutically effective amount of 3-[(3aR,4R,5S,7aS)-5-[(1R)-1-[3,5-bis(trifluoromethyl)phenyl]ethoxy]-4-(4-fluorophenyl)-1,3,3a,4,5,6,7,7a-octahydroisoindol-2-yl]cyclopent-2-en-1-one (serlopitant) or a pharmaceutically acceptable salt, solvate or polymorph thereof to a patient in need of treatment.

17. The method of claim 16, wherein the therapeutically effective amount of serlopitant comprises a dosage of 0.10 mg, 0.15 mg, 0.20 mg, 0.25 mg, 0.5 mg, 0.75 mg, 1 mg, 2 mg, 2.5 mg, 3 mg, 4 mg, 5 mg, 6 mg, 7 mg, 8 mg, 9 mg, 10 mg, 15 mg, 20 mg, 25 mg or 30 mg one or more times a day.

18. The method of claim 17, wherein the therapeutically effective amount of serlopitant comprises a dosage of 1 mg, 3 mg or 5 mg once a day.

19. The method of claim 16, wherein the therapeutically effective amount of serlopitant comprises a dosage of from about 0.1 mg to about 30 mg, or from about 1 mg to about 7.5 mg.

20. The method of claim 16, wherein serlopitant is administered once a day, once every other day, once every third day, once every fourth day, or once a week.

21. The method of claim 16, wherein serlopitant is administered over a period of at least 1 month, 1.5 months or 2 months.

22. The method of claim 16, wherein at least one loading dose of serlopitant is first administered, and at least one therapeutically effective maintenance dose of serlopitant is subsequently administered.

23. The method of claim 22, wherein the at least one loading dose is five times, four times, three times or two times larger than the at least one therapeutically effective maintenance dose.

24. The method of claim 16, wherein serlopitant is administered at bedtime.

25. The method of claim 16, wherein serlopitant is administered orally.

26. The method of claim 16, wherein serlopitant is administered topically.

27. The method of claim 26, wherein serlopitant is administered dermally or transdermally.

28. The method of claim 16, wherein the pruritus is chronic pruritus.

29. The method of claim 16, wherein the CTCL is mycosis fungoides or Sézary's disease.

30. The method of claim 16, further comprising administering one or more additional antipruritic agents.

31. The method of claim 30, wherein the one or more additional antipruritic agents are selected from the group consisting of antihistamines, corticosteroids, immunomodulators, immunosuppressants, opioid receptor antagonists, antidepressants and anticonvulsants.

* * * * *